(12) United States Patent
Kahook et al.

(10) Patent No.: US 10,779,991 B2
(45) Date of Patent: Sep. 22, 2020

(54) OPHTHALMIC KNIFE AND METHODS OF USE

(71) Applicants: The Regents of the University of Colorado, Denver, CO (US); New World Medical, Inc., Rancho Cucamonga, CA (US)

(72) Inventors: Malik Kahook, Denver, CO (US); Khalid Mansour, Corona, CA (US); Suhail Abdullah, Fontana, CA (US); Eric Porteous, Corona, CA (US); Vijay R. Balan, Torrance, CA (US)

(73) Assignees: The Regents of the University of Colorado, a body corporated, Denver, CO (US); New World Medical, Inc., Rancho Cucamonga, CA (US)

( * ) Notice: Subject to any disclaimer, the term of this patent is extended or adjusted under 35 U.S.C. 154(b) by 0 days.

(21) Appl. No.: 16/703,666

(22) Filed: Dec. 4, 2019

(65) Prior Publication Data
US 2020/0107961 A1 Apr. 9, 2020

Related U.S. Application Data

(63) Continuation-in-part of application No. 16/015,078, filed on Jun. 21, 2018, now Pat. No. 10,653,558.
(Continued)

(51) Int. Cl.
*A61F 9/013* (2006.01)
*A61F 9/007* (2006.01)
(Continued)

(52) U.S. Cl.
CPC .... *A61F 9/0133* (2013.01); *A61B 17/320068* (2013.01); *A61F 9/00745* (2013.01);
(Continued)

(58) Field of Classification Search
CPC .. A61F 9/00754; A61F 9/0133; A61B 17/285; A61B 17/3211; A61B 2017/32113
See application file for complete search history.

(56) References Cited

U.S. PATENT DOCUMENTS 2,130,949 A 9/1938 Collens
3,776,238 A 12/1973 Peyman
(Continued)

FOREIGN PATENT DOCUMENTS

EP 0073803 7/1985
EP 1455698 9/2004
(Continued)

OTHER PUBLICATIONS

Anderson, "Trabeculotomy compared to goniotomy for glaucoma in children," Ophthalmology, 1983, 90(7), pp. 805-806.
(Continued)

*Primary Examiner* — Todd J Scherbel
(74) *Attorney, Agent, or Firm* — Morgan, Lewis & Bockius LLP

(57) ABSTRACT

The present invention relates to an ophthalmic knife and methods of its use for treatment of various conditions including eye diseases, such as glaucoma, using minimally invasive surgical techniques. The invention relates to a multi-blade device for cutting the tissues within the eye, for example, a trabecular meshwork (TM).

20 Claims, 15 Drawing Sheets

Related U.S. Application Data which is a continuation of application No. 15/389,328, filed on Dec. 22, 2016, now Pat. No. 10,213,342.

(60) Provisional application No. 62/387,351, filed on Dec. 23, 2015.

(51) Int. Cl.
*A61B 17/32* (2006.01)
*A61B 17/00* (2006.01)
*A61B 17/3211* (2006.01)

(52) U.S. Cl.
CPC ....... *A61F 9/00781* (2013.01); *A61B 17/3211* (2013.01); *A61B 2017/00867* (2013.01); *A61B 2017/320082* (2017.08); *A61B 2217/005* (2013.01); *A61F 9/00736* (2013.01)

(56) References Cited

U.S. PATENT DOCUMENTS

| | | | |
|---|---|---|---|
| 3,882,872 A | 5/1975 | Douvas et al. | |
| 4,011,869 A | 3/1977 | Seiler, Jr. | |
| 4,111,207 A | 9/1978 | Seiler, Jr. | |
| 4,373,530 A * | 2/1983 | Kilejian | A61B 17/0469 606/145 |
| 4,428,748 A | 1/1984 | Peyman et al. | |
| 4,501,274 A | 2/1985 | Skjaerpe | |
| 4,559,942 A | 12/1985 | Eisenberg | |
| 4,577,629 A | 3/1986 | Martinez | |
| 4,649,919 A | 3/1987 | Thimsen et al. | |
| 4,682,597 A | 7/1987 | Myers | |
| 4,900,300 A | 2/1990 | Lee | |
| 5,042,008 A | 8/1991 | Iwasa et al. | |
| 5,163,433 A | 11/1992 | Kagawa et al. | |
| 5,217,476 A | 6/1993 | Wishinsky | |
| 5,222,959 A | 6/1993 | Anis | |
| 5,224,950 A | 7/1993 | Prywes | |
| 5,342,370 A * | 8/1994 | Simon | A61F 9/00781 128/898 |
| 5,364,409 A * | 11/1994 | Kuwabara | A61B 17/0483 606/148 |
| 5,431,671 A | 7/1995 | Nallakrishnan | |
| 5,478,338 A | 12/1995 | Reynard | |
| 5,487,747 A | 1/1996 | Stagmann et al. | |
| 5,558,637 A | 9/1996 | Allonen et al. | |
| 5,569,283 A | 10/1996 | Green et al. | |
| 5,620,453 A | 4/1997 | Nallakrishnan | |
| 5,674,233 A | 10/1997 | Dybbs | |
| 5,713,915 A | 2/1998 | Van Heugten et al. | |
| 5,817,115 A | 10/1998 | Nigam | |
| 5,865,831 A | 2/1999 | Cozean et al. | |
| 6,013,049 A | 1/2000 | Rockley et al. | |
| 6,139,559 A | 10/2000 | Nordan et al. | |
| 6,213,997 B1 | 4/2001 | Hood et al. | |
| 6,241,721 B1 | 6/2001 | Cozean et al. | |
| 6,251,103 B1 | 6/2001 | Berlin | |
| 6,264,668 B1 | 7/2001 | Prywes | |
| 6,388,043 B1 | 5/2002 | Langer et al. | |
| 6,428,501 B1 | 8/2002 | Reynard | |
| 6,497,712 B1 | 12/2002 | Feaster | |
| 6,503,262 B1 | 1/2003 | Edens | |
| 6,720,402 B2 | 4/2004 | Langer et al. | |
| 6,759,481 B2 | 7/2004 | Tong | |
| 6,979,328 B2 | 12/2005 | Baerveldt et al. | |
| 7,374,566 B1 | 5/2008 | Schossau | |
| 7,604,663 B1 | 10/2009 | Reimink et al. | |
| 7,632,303 B1 | 12/2009 | Stalker et al. | |
| 7,648,591 B2 | 1/2010 | Furst et al. | |
| 7,785,321 B2 | 8/2010 | Baerveldt et al. | |
| 7,883,519 B2 * | 2/2011 | Oren | A61B 17/0483 606/148 |
| 7,935,131 B2 | 5/2011 | Anthamatten et al. | |
| 7,955,387 B2 | 6/2011 | Richter | |
| 7,959,641 B2 | 6/2011 | Sorensen et al. | |
| 8,038,923 B2 | 10/2011 | Berger et al. | |
| 9,757,279 B2 | 9/2017 | Kahook | |
| 9,872,799 B2 | 1/2018 | Kahook | |
| 2001/0029386 A1 | 10/2001 | Matsutani et al. | |
| 2002/0026205 A1 | 2/2002 | Matsutani et al. | |
| 2002/0111608 A1 | 8/2002 | Baerveldt et al. | |
| 2003/0208217 A1 | 11/2003 | Dan | |
| 2005/0015104 A1 * | 1/2005 | Morawski | A61B 17/3211 606/167 |
| 2005/0070941 A1 | 3/2005 | Isogimi | |
| 2005/0113644 A1 | 5/2005 | Obenchain et al. | |
| 2005/0216019 A1 | 9/2005 | Eckman | |
| 2006/0015128 A1 | 1/2006 | Fard | |
| 2006/0106370 A1 | 5/2006 | Baerveldt et al. | |
| 2006/0149194 A1 | 7/2006 | Conston et al. | |
| 2006/0241580 A1 | 10/2006 | Mittelstein et al. | |
| 2006/0271074 A1 | 11/2006 | Ewers et al. | |
| 2007/0073275 A1 | 3/2007 | Conston et al. | |
| 2007/0100363 A1 | 5/2007 | Dollar et al. | |
| 2007/0276420 A1 | 11/2007 | Sorensen et al. | |
| 2009/0248141 A1 | 10/2009 | Shandas et al. | |
| 2009/0287233 A1 | 11/2009 | Huculak | |
| 2009/0306689 A1 | 12/2009 | Welty et al. | |
| 2010/0152609 A1 | 6/2010 | Zwolinski et al. | |
| 2010/0268175 A1 * | 10/2010 | Lunsford | A61B 17/320725 604/272 |
| 2011/0077626 A1 | 3/2011 | Baerveldt et al. | |
| 2011/0202049 A1 | 8/2011 | Jia et al. | |
| 2011/0230877 A1 | 9/2011 | Huculak | |
| 2012/0083727 A1 | 4/2012 | Barnett | |
| 2012/0239056 A1 | 9/2012 | Dijkman et al. | |
| 2014/0030273 A1 | 1/2014 | Verploegen et al. | |
| 2014/0121697 A1 | 5/2014 | Scheller et al. | |
| 2015/0045820 A1 | 2/2015 | Kahook | |
| 2016/0354248 A1 | 12/2016 | Kahook | |
| 2017/0181892 A1 | 6/2017 | Kahook et al. | |
| 2017/0367890 A1 | 12/2017 | Kahook | |
| 2018/0133056 A1 | 5/2018 | Kahook | |

FOREIGN PATENT DOCUMENTS

| | | |
|---|---|---|
| EP | 1615604 | 1/2006 |
| EP | 2303203 | 4/2011 |
| KR | 1020040058309 | 9/2004 |
| WO | WO-9306800 | 4/1993 |
| WO | WO-2001078631 | 10/2001 |
| WO | WO-2003045290 | 6/2003 |
| WO | WO-2004093761 | 11/2004 |
| WO | WO-2004110501 | 12/2004 |
| WO | WO-2009140185 | 11/2009 |
| WO | WO-2011030081 | 3/2011 |
| WO | WO-2012044952 | 4/2012 |
| WO | WO-201213718 | 10/2012 |
| WO | WO-2013163034 | 10/2013 |
| WO | WO-2017112893 | 6/2017 |

OTHER PUBLICATIONS

Ellingsen, Bruce A. et al., "Trabeculotomy and sinusotomy in enucleated human eyes", Investigative Ophthalmology & Visual Science Jan. 1972, vol. 11, Issue 1, pp. 21-28, downloaded from iovs.arvojournals.org on Feb. 23, 2019.

European Office Action for Application No. 13781487.7, dated Dec. 20, 2018, 4 pages.

Extended European Search Report and Written Opinion for Application No. 16880112.4, dated Aug. 2, 2019, 6 pages.

Francis et al., "Ab interno trabeculectomy: development of a novel device (Trabectome®) and surgery for open-angle glaucoma," Journal of Glaucoma, 2006, 15(1), pp. 68-73.

Grant, "Clinical measurements of aqueous outflow," AMA Archives of Ophthalmology, 1951, 46(2), pp. 113-131.

Grant, "Experimental aqueous perfusion in enucleated human eyes," Archives of Ophthalmology, 1963, 69(6), pp. 783-801.

Grant, Morton W., "Symposium: Micorsurgery of the Ouflow Channels", Trans Am Acad Ophthalmol Otolaryngol. Mar.-Apr. 1972;76(2):398-404.

(56) References Cited

OTHER PUBLICATIONS

Herschler et al., "Modified goniotomy for inflammatory glaucoma. Histologic evidence for the mechanism of pressure reduction," Archives of Ophthalmology, 1980, 98(4), pp. 684-687.
International Search Report and Written Opinion for Application No. PCT/US2016/068393, dated Apr. 17, 2017, 29 pages.
International Search Report and Written Opinion for Application No. PCT/US2018/056935, dated Jan. 31, 2019, 12 pages.
Jacobi et al., "Goniocurettage for removing trabecular meshwork: clinical results of a new surgical technique in advanced chronic open-angle glaucoma," American Journal of Ophthalmology, 1999, 125(5), pp. 505-510.
Jacobi et al., "Technique of goniocurettage: a potential treatment for advanced chronic open angle glaucoma," British Journal of Ophthalmology, 1997, 81(4) pp. 302-307.
Jea et al., "Ab Interno Trabeculectomy Versus Trabeculectomy for Open-Angle Glaucoma," Ophthalmology, 2012, 119(1), pp. 36-42.
Johnson et al., "Human trabecular meshwork organ culture. A new method," Investigative Ophthalmology & Visual Science, 1987, 26(6), pp. 945-953.
Luntz et al., "Trabeculotomy ab externo and trabeculectomy in congenital and adult-onset glaucoma," American Journal of Ophthalmology, 1977, 83(2), pp. 174-179.
M. Johnstone et al., "Microsurgery of Schlemm's Canal and the Human Aqueous Outflow System," Am. J. Ophthalmology 76(6):906-917 (1973) ("Johnstone 1973").
Manuel Quintana, *Gonioscopic Trabeculotomy. First Results*, in 43 Second European Glaucoma Symposium, Documenta Ophthalmologica Proceedings Series 265 (E.L. Greve, W. Leydhecker, & C. Raitta ed., 1985) ("Quintana 1985").
Minckler et al., "Clinical Results with the Trabectome® for Treatment of Open-Angle Glaucoma," Ophthalmology, 2005, 112(6), pp. 962-967.
Pantcheva et al., "Ab Interno Trabeculectomy," Middle East African Journal of Ophthalmology, 2010, 17(4), pp. 287-289.
PCT International Search Report of International Application No. PCT/US2013/037374 dated Jul. 25, 2013.
Quigley et al., "The number of people with glaucoma worldwide in 2010 and 2020," British Journal of Ophthalmology, 2006, 90(3), pp. 262-267.
Seibold et al., "Preclinical Investigation of Ab Interno Trabeculectomy Using a Novel Dual-Blade Device," American Journal of Ophthalmology, 2013, 155(3), pp. 524-529.e522.
Supplementary European Search Report for Application No. 13781487.7, dated Jul. 9, 2015, 7 pages.
Tan et al., "Postoperative complications after glaucoma surgery for primary angle-closure glaucoma vs primary open-angle glaucoma," Archives of Ophthalmology, 2011, 129(8), pp. 987-992.
Ting et al., "Ab interno trabeculectomy: Outcomes in exfoliation versus primary open-angle glaucoma," Journal of Cataract & Refractive Surgery, 2012, 38(2), pp. 315-313.

\* cited by examiner

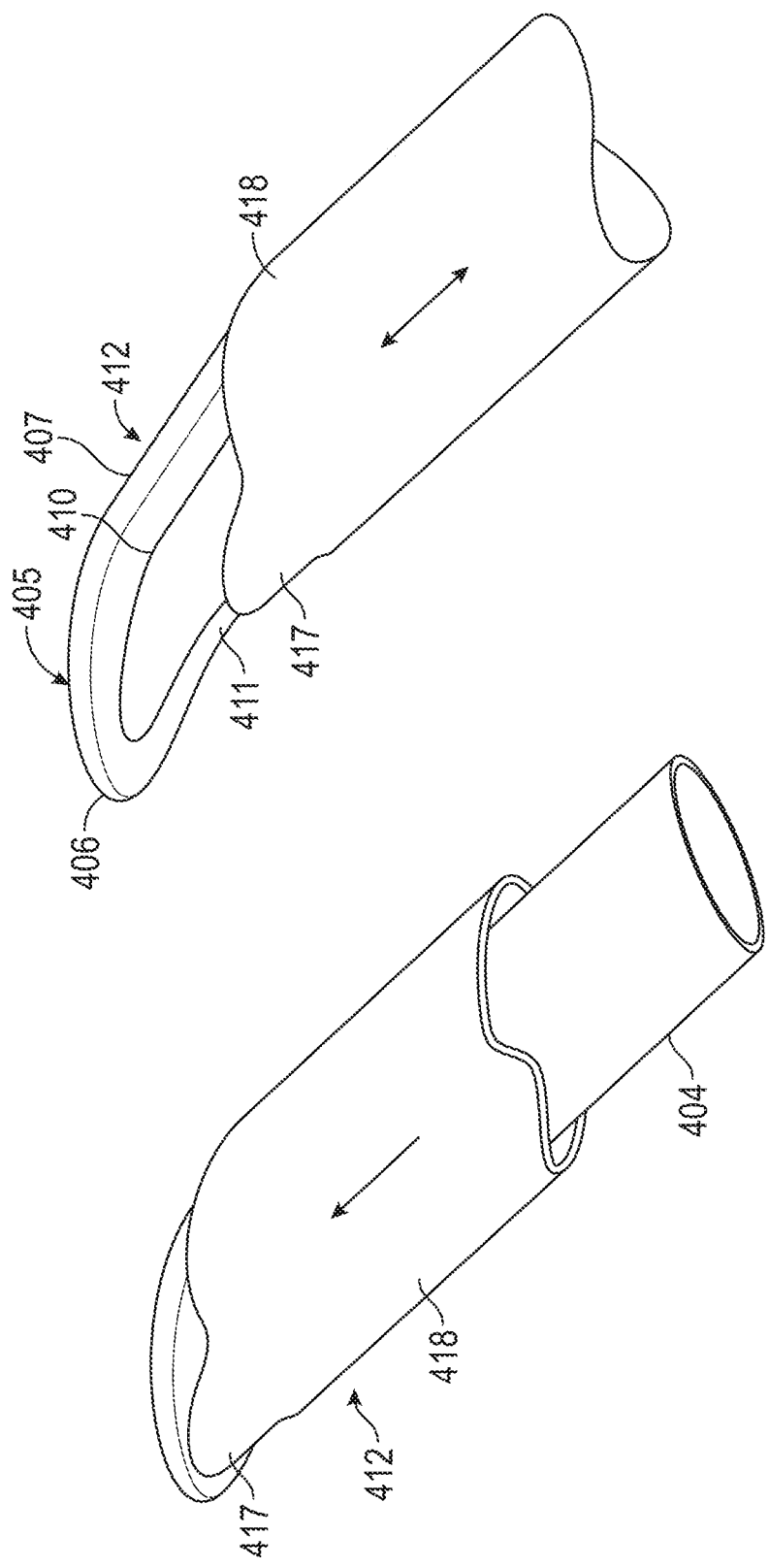

OPHTHALMIC KNIFE AND METHODS OF USE

CROSS-REFERENCE TO RELATED APPLICATIONS

This application is a continuation-in-part of U.S. patent application Ser. No. 16/015,078, filed on Jun. 21, 2018, issued as U.S. Pat. No. 10,653,558 on May 19, 2020, which is a continuation of U.S. patent application Ser. No. 15/389,328, filed Dec. 22, 2016, issued as U.S. Pat. No. 10,213,342 on Feb. 26, 2019, which is a nonprovisional patent application of and claims the benefit to U.S. Provisional Patent Application No. 62/387,351, filed Dec. 23, 2015 and titled "Ophthalmic knife and methods of use."

FIELD OF THE INVENTION

The present invention relates to an ophthalmic knife and methods of its use for treatment of various conditions including eye diseases, such as glaucoma, using minimally invasive surgical techniques. An ophthalmic knife can be used for cutting the tissues within the eye, for example, a trabecular meshwork (TM). This invention also relates to surgical medicinal intervention. For example, the present invention relates to a microsurgical device and methods of its use for treatment of various medical conditions including but not limited to eye diseases, such as glaucoma, using minimally invasive surgical techniques.

BACKGROUND OF THE INVENTION

There are numerous medical and surgical procedures in which it is desirable to cut and remove a strip of tissue of controlled width from the body of a human or veterinary patient. For example, it may sometimes be desirable to form an incision of a controlled width (e.g., an incision that is wider than an incision made by a typical scalpel, cutting blade or needle) in the eye, skin, mucous membrane, tumor, organ or other tissue or a human or animal. In addition, it may sometimes be desirable to remove a strip or quantity of tissue from the body of a human or animal for use as a biopsy specimen, for chemical/biological analysis, for retention or archival of DNA identification purposes, etc. In addition, some surgical procedures require removal of a strip of tissue of a known width from an anatomical location within the body of a patient. One surgical procedure wherein a strip of tissue of a known width is removed from an anatomical location within the body of a patient is an ophthalmological procedure used to treat glaucoma. This ophthalmological procedure is sometimes referred to as a gonioctomy. In a gonioctomy procedure, a device that is operative to cut or ablate a strip of tissue of approximately 2-10 mm in length or more and about 50-200 µm in width is inserted into the anterior chamber of the eye and used to remove a full thickness strip of tissue from the trabecular meshwork. At present there remains a need in the art for the development of simple, inexpensive and accurate instruments useable to perform the procedure of cutting the trabecular meshwork (TM) in the eye and effectively remove a complete full thickness strip of TM without leaving TM leaflets as well as other procedures where it is desired to remove a strip of tissue from a larger mass of tissue.

SUMMARY OF THE INVENTION

The present invention relates to an ophthalmic knife and methods of its use for treatment of various conditions including eye diseases, such as glaucoma, using minimally invasive surgical techniques. An ophthalmic knife can be used for cutting the tissues within the eye, for example, a trabecular meshwork (TM). This invention also relates to surgical medicinal intervention. For example, the present invention relates to a microsurgical device and methods of its use for treatment of various medical conditions including but not limited to eye diseases, such as glaucoma, using minimally invasive surgical techniques.

In one embodiment, the present invention contemplates a dual platform/dual-blade ophthalmic knife comprising a handle connected to a shaft, said shaft connected to a first platform and a second platform, said first platform comprising a first and second blade and a first anterior blade tip and said second platform comprising a third and fourth blade and a second anterior blade tip. In one embodiment, the anterior blade tip is a retractable blade tip. In one embodiment, said first and second anterior blade tips are retractable blade tips. In one embodiment, the anterior blade tip is a wedge blade tip. In one embodiment, the first blade and a second blade are attached to a first lateral side and a second lateral side (respectively) of the first platform. In one embodiment, the third blade and a fourth blade are attached to a third lateral side and a fourth lateral side (respectively) of the second platform. In one embodiment, the first platform and second platform are configured at a 180° angle. In one embodiment, said blade tips comprise right triangles. In one embodiment, said right triangle follows the Pythagoras' theorem formula $(a^2+b^2=c^2)$ wherein the sides of said tip comprise length a and b and the length of the hypotenuse is c. 8. In one embodiment, said platforms each comprises a ramp. In one embodiment, said distal end of said platform ramps up from the piercing blade towards to parallel blades. In one embodiment, said distal end of said platform ramps up from the piercing blade towards to parallel blades that are positioned above the level of the TM. In one embodiment, the first and second platform are offset. In one embodiment, the first platform and second platform are parallel. In one embodiment, the first platform comprises a first ramp increasing in depth extending from the first anterior blade tip to a first posterior end. In one embodiment, the second platform comprises a second ramp increasing in depth extending from the second anterior blade tip to a second posterior end. In one embodiment, the first and second blades are parallel. In one embodiment, the first and second blade are at an angle. In one embodiment, the platform comprises an annular cutting edge. In one embodiment, the third and fourth blades are parallel. In one embodiment, the third and fourth blades are at an angle. In one embodiment, the first platform comprises an annular cutting edge. In one embodiment, the second platform comprises an annular cutting edge. In one embodiment, the first and second lateral blades are retractable and attached within a first and second platform cavity (respectively). In one embodiment, the third and fourth lateral blades are retractable and attached within a third and fourth platform cavity (respectively). In one embodiment, the handle comprises a lateral blade actuator switch in operable communication with the first, second, third and fourth platform cavities. In one embodiment, the platform further comprises a grasping feature. In one embodiment, said parallel dual platforms can be actuated to come together to grasp tissue. In one embodiment, the grasping feature includes but is not limited to, a tweezer element or a forcep element. In one embodiment, parallel dual platforms can be actuated to come together to grasp tissue. In one embodiment, the grasping feature comprises a sleeve extending over the shaft, wherein the handle comprises a sleeve actuator switch. In one embodiment, the grasping feature is made of a shape-memory material that is retractable into a lumen of the device. In one embodiment, the platform further comprises a slidable punch that can detach tissue from the multi-blade device. In one embodiment, the multi-blade device further comprises at least one lumen extending longitudinally within said handle, shaft and platform. In one embodiment, the lumen comprises an exit port in said platform. In one embodiment, the exit port is on the top surface of the platform. In one embodiment, the exit port is on the bottom surface of the platform. In one embodiment, the lumen comprises an entry port in said handle. In one embodiment, the lumen comprises a viscoelastic fluid. In one embodiment, the lumen comprises an aspiration fluid. In one embodiment, the platform further comprises a through-hole extending from the top surface to the posterior end. In one embodiment, the handle is curved. In one embodiment, the device further comprises a fiber optic visualization system. In one embodiment, the width of the platform is approximately 150-180 microns. In one embodiment, the platform is a color including, but not limited to, blue, white, black, orange and yellow or any combination thereof. In one embodiment, the platform comprises a concave bottom surface. In one embodiment, the shaft comprises an annular ring. In one embodiment, the platform further comprises at least one heating element. In one embodiment, the shaft is a telescoping shaft.

In one embodiment, the present invention contemplates a quad-blade ophthalmic knife comprising a handle connected to a shaft, said shaft connected to a platform comprising four cutting blades and an anterior blade tip. In one embodiment, the anterior blade tip is a retractable blade tip. In one embodiment, the anterior blade tip is a wedge blade tip. In one embodiment, the platform comprises a first blade and a second blade attached to a first lateral side and a second lateral side (respectively) of the platform. In one embodiment, said blade tip comprises a right triangle. In one embodiment, said right triangle follows the Pythagoras' theorem formula $(a^2+b^2=c^2)$ wherein the sides of said tip comprise length a and b and the length of the hypotenuse is c. In one embodiment, said platform comprises a ramp. In one embodiment, said distal end of said platform ramps up from the piercing blade towards to parallel blades. In one embodiment, said distal end of said platform ramps up from the piercing blade towards to parallel blades that are positioned above the level of the TM. In one embodiment, the shaft further comprises a third blade and a fourth blade attached to a first lateral side and a second lateral side (respectively) of the shaft. In one embodiment, the third and fourth blade are slidably engaged with the shaft. In one embodiment, the handle comprises a compressible material that contacts said third and fourth blades. In one embodiment, the shaft is connected to a second quad-blade knife positioned at a 180° angle from the first quad-blade knife. In one embodiment, the shaft is connected to a second quad-blade knife position in parallel to the first quad-blade knife. In one embodiment, the platform comprises a ramp increasing in depth extending from the anterior blade tip to the posterior end. In one embodiment, the first and second blades are parallel. In one embodiment, the first and second blade are at an angle. In one embodiment, the platform comprises an annular cutting edge. In one embodiment, the first and second lateral blades are retractable and attached within a first and second platform cavity (respectively). In one embodiment, the handle comprises a lateral blade actuator switch in operable communication with the first and second platform cavities. In one embodiment, the platform further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the platform further comprises a slidable punch that can detach tissue from the multi-blade device. In one embodiment, the multi-blade device further comprises at least one lumen extending longitudinally within said handle, shaft and platform. In one embodiment, the lumen comprises an exit port in said platform. In one embodiment, the exit port is on the top surface of the platform. In one embodiment, the exit port is on the bottom surface of the platform. In one embodiment, the lumen comprises an entry port in said handle. In one embodiment, the lumen comprises a viscoelastic fluid. In one embodiment, the lumen comprises an aspiration fluid. In one embodiment, the platform further comprises a through-hole extending from the top surface to the posterior end. In one embodiment, the handle is curved. In one embodiment, the device further comprises a fiber optic visualization system. In one embodiment, the width of the platform is approximately 150-180 microns. In one embodiment, the platform is a color including, but not limited to, blue, white, black, orange and yellow or any combination thereof. In one embodiment, the platform comprises a concave bottom surface. In one embodiment, the shaft comprises an annular ring. In one embodiment, the platform further comprises at least one heating element. In one embodiment, the shaft is a telescoping shaft.

In one embodiment, the present invention contemplates an ultrasonic ophthalmic knife comprises a handle, shaft, an anterior blade tip, and platform wherein the platform comprises an ultrasonic emitter and a footplate protecting surrounding tissue from the ultrasonic blades. In one embodiment, the ultrasonic emitter anterior blade tip vibrates in a fixed frequency when the device is actuated. In one embodiment, both longitudinal and lateral motions are possible for the tip. In one embodiment, said ultrasonic emitter has adjustable power settings. In one embodiment, said power settings are optimized to minimize the application of heat during use. The ultrasonic knife allows for tissue cutting while reducing the need to pre-stretch or tension tissue. The knife tip vibrates in a fixed frequency when the device is actuated. Both longitudinal and lateral motions are possible for the tip. Power settings are optimized to minimize the application of heat to the tissue. In one embodiment, the anterior blade tip is a wedge blade tip. In one embodiment, the anterior blade tip is a retractable blade tip. In one embodiment, said blade tip comprises a right triangle. In one embodiment, said right triangle follows the Pythagoras' theorem formula $(a^2+b^2=c^2)$ wherein the sides of said tip comprise length a and b and the length of the hypotenuse is c. In one embodiment, said platform comprises a ramp. In one embodiment, said distal end of said platform ramps up from the piercing blade towards to parallel blades. In one embodiment, said distal end of said platform ramps up from the piercing blade towards to parallel blades that are positioned above the level of the TM. In one embodiment, the platform further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the platform further comprises a slidable punch that can detach tissue from the ultrasonic knife. In one embodiment, the ultrasonic device further comprises at least one lumen extending longitudinally within said handle, shaft and platform. In one embodiment, the lumen comprises an exit port in said platform. In one embodiment, the exit port is on the top surface of the platform. In one embodiment, the exit port is on the bottom surface of the platform. In one embodiment, the lumen comprises an entry port in said handle. In one embodiment, the lumen comprises a viscoelastic fluid. In one embodiment, the lumen comprises an aspiration fluid. In one embodiment, the platform further comprises a through-hole extending from the top surface to the posterior end. In one embodiment, the handle is curved. In one embodiment, the ultrasonic device further comprises a fiber optic visualization system. In one embodiment, the width of the platform is approximately 150-180 microns. In one embodiment, the platform is a color including, but not limited to, blue, white, black, orange and yellow or any combination thereof. In one embodiment, the platform comprises a concave bottom surface. In one embodiment, the shaft comprises an annular ring. In one embodiment, the platform further comprises at least one heating element. In one embodiment, the shaft is a telescoping shaft.

In one embodiment, the present invention contemplates a pincer ophthalmic knife comprising a handle connected to a shaft, said shaft connected to a lower platform and an upper platform. In one embodiment, the lower platform comprises an anterior blade tip. In one embodiment, the anterior blade tip is a wedge blade tip. In one embodiment, the shaft and the upper platform are connected by a hinge. In one embodiment, the lower platform comprises a first lateral side attached to a first blade and a second lateral side attached to a second blade. In one embodiment, the upper platform comprises a first slot and a second slot, wherein the first and second slots are positioned above said first and second blades. In one embodiment, the lower platform further comprises an anterior blade tip. In one embodiment, said blade tip comprises a right triangle. In one embodiment, said right triangle follows the Pythagoras' theorem formula ($a^2+b^2=c^2$) wherein the sides of said tip comprise length a and b and the length of the hypotenuse is c. In one embodiment, said platform comprises a ramp. In one embodiment, said distal end of said platform ramps up from the piercing blade towards to parallel blades. In one embodiment, said distal end of said platform ramps up from the piercing blade towards to parallel blades that are positioned above the level of the TM. In one embodiment, the lower platform is at least 8 mm in length. In one embodiment, the platform further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the platform further comprises a slidable punch that can detach tissue from the pincer ophthalmic knife. In one embodiment, the pincer ophthalmic knife device further comprises at least one lumen extending longitudinally within said handle, shaft and platform. In one embodiment, the lumen comprises an exit port in said platform. In one embodiment, the exit port is on the top surface of the platform. In one embodiment, the exit port is on the bottom surface of the platform. In one embodiment, the lumen comprises an entry port in said handle. In one embodiment, the lumen comprises a viscoelastic fluid. In one embodiment, the lumen comprises an aspiration fluid. In one embodiment, the platform further comprises a through-hole extending from the top surface to the posterior end. In one embodiment, the handle is curved. In one embodiment, the pincer ophthalmic knife device further comprises a fiber optic visualization system. In one embodiment, the width of the platform is approximately 150-180 microns. In one embodiment, the platform is a color including, but not limited to, blue, white, black, orange and yellow or any combination thereof. In one embodiment, the platform comprises a concave bottom surface. In one embodiment, the shaft comprises an annular ring. In one embodiment, the platform further comprises at least one heating element. In one embodiment, the shaft is a telescoping shaft.

In one embodiment, the present invention contemplates a gripping ophthalmic knife comprising a handle connected to a shaft, said shaft comprises an first lateral alligator clip and a second lateral alligator clip, a platform connected to the shaft, said platform comprising a first lateral blade and a second lateral blade, and an anterior blade tip. In one embodiment, the anterior blade tip is a wedge blade tip. In one embodiment, the anterior blade tip is a retractable blade tip. In one embodiment, said blade tip comprises a right triangle. In one embodiment, said right triangle follows the Pythagoras' theorem formula ($a^2+b^2=c^2$) wherein the sides of said tip comprise length a and b and the length of the hypotenuse is c. In one embodiment, said platform comprises a ramp. In one embodiment, said distal end of said platform ramps up from the piercing blade towards to parallel blades. In one embodiment, said distal end of said platform ramps up from the piercing blade towards to parallel blades that are positioned above the level of the TM. In one embodiment, the first lateral blade and the second lateral blade are attached to a first lateral side and a second lateral side (respectively) of the platform. In one embodiment, the first lateral alligator clip comprises a first serrated jaw and a second serrated jaw. In one embodiment, the second lateral alligator clip comprises a first serrated jaw and a second serrated jaw. In one embodiment, the first and second serrated jaws of the first lateral alligator clip are hinged. In one embodiment, the first and second serrated jaws of the second lateral alligator clip are hinged. In one embodiment, the handle comprises a compressible material that contacts said first and second alligator clips. In one embodiment, the platform further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the platform further comprises a slidable punch that can detach tissue from the multi-blade device. In one embodiment, the multi-blade device further comprises at least one lumen extending longitudinally within said handle, shaft and platform. In one embodiment, the lumen comprises an exit port in said platform. In one embodiment, the exit port is on the top surface of the platform. In one embodiment, the exit port is on the bottom surface of the platform. In one embodiment, the lumen comprises an entry port in said handle. In one embodiment, the lumen comprises a viscoelastic fluid. In one embodiment, the lumen comprises an aspiration fluid. In one embodiment, the platform further comprises a through-hole extending from the top surface to the posterior end. In one embodiment, the handle is curved. In one embodiment, the device further comprises a fiber optic visualization system. In one embodiment, the width of the platform is approximately 150-180 microns. In one embodiment, the platform is a color including, but not limited to, blue, white, black, orange and yellow or any combination thereof. In one embodiment, the platform comprises a concave bottom surface. In one embodiment, the shaft comprises an annular ring. In one embodiment, the platform further comprises at least one heating element. In one embodiment, the shaft is a telescoping shaft.

In one embodiment, the present embodiment contemplates a lancet ophthalmic knife comprising a handle connected to a shaft, said shaft connected to a wire element. In one embodiment, the wire element comprises a geometric shape including, but not limited to, a triangle, square, a rectangular, an octagon, a circle, an ellipse or an oval. In one embodiment, the wire element comprises a first wire end and second wire end. In one embodiment, the first wire end is connected to the shaft at a first position. In one embodiment, the second wire end is connected to the shaft at a second position. In one embodiment, the shaft further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the shaft further comprises a slidable punch that can detach tissue from the wire element. In one embodiment, the lancet knife further comprises at least one lumen extending longitudinally within said handle and shaft. In one embodiment, the lumen comprises an exit port in said shaft. In one embodiment, the lumen comprises an entry port in said handle. In one embodiment, the lumen comprises a viscoelastic fluid. In one embodiment, the lumen comprises an aspiration fluid. In one embodiment, the handle is curved. In one embodiment, the device further comprises a fiber optic visualization system. In one embodiment, the wire element is a color including, but not limited to, blue, white, black, orange and yellow or any combination thereof. In one embodiment, the shaft comprises an annular ring. In one embodiment, the wire element further comprises at least one heating element. In one embodiment, the shaft is a telescoping shaft.

In one embodiment, the present invention contemplates an axial blade ophthalmic knife comprising a handle connected to a shaft, said shaft connected to a first and second blade. In one embodiment, the first and second blade extend axially from the shaft. In one embodiment, a shaft overhang is positioned between the first and second blades and the lateral edges of the shaft. The overhang is positioned so as to limit the depth of cut made by the blades. In one embodiment, the shaft further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the shaft further comprises a slidable punch that can detach tissue from the shaft. In one embodiment, the ophthalmic knife further comprises at least one lumen extending longitudinally within said handle and shaft. In one embodiment, the lumen comprises an exit port in said shaft. In one embodiment, the lumen comprises an entry port in said handle. In one embodiment, the lumen comprises a viscoelastic fluid. In one embodiment, the lumen comprises an aspiration fluid. In one embodiment, the handle is curved. In one embodiment, the device further comprises a fiber optic visualization system. In one embodiment, the shaft is a color including, but not limited to, blue, white, black, orange and yellow or any combination thereof. In one embodiment, the shaft comprises an annular ring. In one embodiment, the first and second blades further comprise at least one heating element. In one embodiment, the shaft is a telescoping shaft.

In one embodiment, the present invention contemplates a V-blade ophthalmic knife comprising a handle connected to a shaft comprising a first blade, said shaft connected to a platform, wherein the first blade overhangs said platform such that the first blade and said platform are connected at an angle. In one embodiment, the platform further comprises an anterior blade tip. In one embodiment, the anterior blade tip is a retractable blade tip. In one embodiment, the anterior blade tip is a wedge blade tip. In one embodiment, said blade tip comprises a right triangle. In one embodiment, said right triangle follows the Pythagoras' theorem formula ($a^2 + b^2 = c^2$) wherein the sides of said tip comprise length a and b and the length of the hypotenuse is c. In one embodiment, said platform comprises a ramp. In one embodiment, said distal end of said platform ramps up from the piercing blade towards to parallel blades. In one embodiment, said distal end of said platform ramps up from the piercing blade towards to parallel blades that are positioned above the level of the TM. In one embodiment, the platform comprises a ramp increasing in depth extending from the anterior blade tip to the posterior end. In one embodiment, the platform comprises a ramp increasing in depth extending from the anterior blade tip to the posterior end. In one embodiment, the platform comprises an annular cutting edge. In one embodiment, the shaft further comprises a grasping feature. In one embodiment, the grasping feature includes but is not limited to, a tweezer element or a forcep element. In one embodiment, the grasping feature comprises a sleeve extending over the shaft, wherein the handle comprises a sleeve actuator switch. In one embodiment, the shaft further comprises a slidable punch that can detach tissue from the shaft. In one embodiment, the ophthalmic knife further comprises at least one lumen extending longitudinally within said handle and shaft. In one embodiment, the lumen comprises an exit port in said shaft. In one embodiment, the lumen comprises an entry port in said handle. In one embodiment, the lumen comprises a viscoelastic fluid. In one embodiment, the lumen comprises an aspiration fluid. In one embodiment, the handle is curved. In one embodiment, the device further comprises a fiber optic visualization system. In one embodiment, the shaft is a color including, but not limited to, blue, white, black, orange and yellow or any combination thereof. In one embodiment, the shaft comprises an annular ring. In one embodiment, the first and second blades further comprise at least one heating element. In one embodiment, the shaft is a telescoping shaft.

In one embodiment, the present invention contemplates, a method for using an ophthalmic knife, comprising: a) providing an ophthalmic knife selected from the group consisting of a dual platform/dual blade ophthalmic knife, a quad-blade ophthalmic knife, an ultrasonic ophthalmic knife, a pincer ophthalmic knife, a gripping ophthalmic knife, a lancet ophthalmic knife, an axial blade ophthalmic knife and a V-blade ophthalmic knife; b) advancing said ophthalmic knife through an incision to a tissue target site; and c) cutting a strip of tissue from said target site. In one embodiment, the knife is integrated into an endoscope. In one embodiment, the method further comprises visualizing said cutting with a fiber optic visualization system. In one embodiment, the tissue target site is located within the body of a patient. In one embodiment, the method further comprises the step of removing said strip of tissue from said tissue target site. In one embodiment, the method further comprises the step of treating said patient for glaucoma. In one embodiment, the treating comprises draining aqueous humor from the eye of said subject. In one embodiment, said advancing further comprises; i) inserting said knife into an ocular anterior chamber; and ii) positioning said knife adjacent to, or within, a trabecular meshwork of the eye. In one embodiment, said incision is in an anatomical location selected from the group consisting of an eyeball, skin, mucous membrane, an organ, and a tumor.

According to some embodiments, disclosed is a dual-blade ophthalmic knife, comprising: a handle; a shaft connected to the handle; and a platform connected to the shaft, wherein the platform comprises: a first blade; a second blade; an anterior blade tip; and an extension member, wherein the extension member is configured as a grasping feature.

The ophthalmic knife may further comprise wherein the grasping feature is a tweezer or a forceps. The grasping feature may comprise spring biased to close the grasping feature. The anterior blade tip may be a retractable blade tip. The first blade and the second blade may be respectively attached to a first lateral side and a second lateral side of the platform. The platform may comprise a ramp increasing in depth extending from the anterior blade tip to a posterior end. The platform may further comprise a first annular cutting edge. A width a the platform may be between 0.2 to 0.3 mm. The shaft may be a telescoping shaft. The ophthalmic knife may further comprise a movable sleeve configured to slidably move along the shaft. The sleeve may be configured to overcome a biasing force of the grasping feature by engaging at least a portion of the grasping feature as the sleeve is moved in a direction along the shaft. The handle may comprise an activation member coupled to the sleeve, the activation member configured to cause the sleeve to move. At least a portion of the grasping feature may comprise a sharpened surface configured to cut tissue.

According to some embodiments, disclosed is a method for incising a trabecular meshwork to form an opening in trabecular meshwork tissue of an eye having a Schlemm's Canal, an anterior chamber and a trabecular meshwork. The method may comprise providing a dual-blade ophthalmic knife, comprising: a handle; a shaft connected to the handle; and a platform connected to the shaft, wherein the platform comprises: a first blade; a second blade; an anterior blade tip; and an extension member, wherein the extension member is configured as a grasping feature. The method may further comprise inserting the platform into the anterior chamber, the platform including the anterior tip; advancing the platform, anterior tip first, through the trabecular meshwork and into the Schlemm's Canal; advancing the platform, anterior tip first, through the Schlemm's Canal such that trabecular meshwork tissue contacts and is severed by the first and second blades; and grasping the severed trabecular meshwork tissue with the grasping feature.

The method may comprise wherein the grasping feature is a tweezer or a forceps. The method may comprise wherein the grasping feature comprises a spring biased to close the grasping feature. The method may comprise wherein the platform of the device further comprises a bottom surface that is transversely concave, wherein the platform is configured so that when the platform is advanced into the Schlemm's Canal, a back wall of the Schlemm's canal is juxtaposed to the bottom surface. The method may comprise wherein the handle of the device comprises an activation member, wherein applying a force to the activation member causes the grasping feature to close. The method may comprise wherein the handle of the device comprises an activation member, wherein applying a force to the activation member causes the grasping feature to open.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

The inventive subject matter disclosed herein is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "therapeutically effective amounts" or "pharmaceutically effective amounts", as used herein means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein "goniotomy" refers to a surgical procedure primarily used to treat congenital glaucoma or other types of glaucoma.

As used herein "trabecular meshwork" refers to area of tissue in the eye located around the base of the cornea, near the ciliary body, (between the scleral spur and schwalbe's line) and is responsible for draining the aqueous humor from the eye via the anterior chamber (the chamber on the front of the eye covered by the cornea). The tissue is spongy and lined by trabeculocytes; it allows fluid to drain into a set of tubes called Schlemm's canal and eventually flowing into the blood system.

As used herein "Schlemm's canal" refers to a circular channel in the eye that collects aqueous humor from the anterior chamber and delivers it into the bloodstream via the collector channels and anterior ciliary veins.

As used herein "eye diseases" refers to various conditions of the eye including, but not limited to Glaucoma—optic neuropathy, Glaucoma suspect—ocular hypertension, Primary open-angle glaucoma, Primary angle-closure glaucoma, primary open angle glaucoma, normal or low tension glaucoma, pseudoexfoliation glaucoma, pigment dispersion glaucoma, angle closure glaucoma (acute, subacute, chronic), neovascular or inflammatory glaucoma, ocular hypertension, and other types of glaucoma that are related to dysregulation of intraocular pressure As used herein "hypotony" refers to reduced intraocular pressure. The statistical definition of hypotony is intraocular pressure (IOP) less than 6.5 mmHg, which is more than 3 standard deviations below the mean IOP. The clinical definition of hypotony is IOP low enough to result in pathology (vision loss). The vision loss from low IOP may be caused by corneal edema, astigmatism, cystoid macular edema, maculopathy, or other condition. Hypotony maculopathy is characterized by a low IOP associated with fundus abnormalities, including chorioretinal folds, optic nerve head edema in the acute setting, and vascular tortuosity.

As used herein "Schwalbe's line" refers to the anatomical line found on the interior surface of the eye's cornea, and delineates the outer limit of the corneal endothelium layer. Specifically, it represents the termination of Descemet's membrane.

As used herein "descemet's membrane" refers to the basement membrane that lies between the corneal proper substance, also called stroma, and the endothelial layer of the cornea.

As used herein "scleral spur" refers to an annular structure composed of collagen in the human eye, a protrusion of the sclera into the anterior chamber. It is the origin of the longitudinal fibres of the ciliary muscle and is attached anteriorly to the trabecular meshwork. Open-angle glaucoma (OAG) and closed-angle glaucoma (CAG) may be treated by muscarinic receptor agonists (e.g., pilocarpine), which cause rapid miosis and contraction of the ciliary muscles, this pulls the scleral spur and results in the trabecular meshwork being stretched and separated. This opens the fluid pathways and facilitates drainage of the aqueous humour into the canal of Schlemm and ultimately decreasing intraocular pressure.

As used herein "Trabectome®" refers to a minimally invasive glaucoma surgical tool for the surgical management of adult, juvenile and infantile glaucoma. Unlike a trabeculectomy, the surgery with a Trabectome® should not create an external filtering bleb or require leaving a permanent hole in the eye. Instead, the Trabectome® electosurgical handpiece opens access to the eyes natural drainage system. This procedure is performed through a small incision similar to that of cataract surgery and allows the patient to go home on the same day.

BRIEF DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 4A depicts bi-directional configuration 35 of two platforms configured at a 180° angle.

FIG. 20A shows a perspective view of a device in a sheathed position according to embodiments of the present disclosure.

FIG. 20B shows a perspective view of the device of FIG. 34A in an unsheathed position according to embodiments of the present disclosure.

Figure 1:
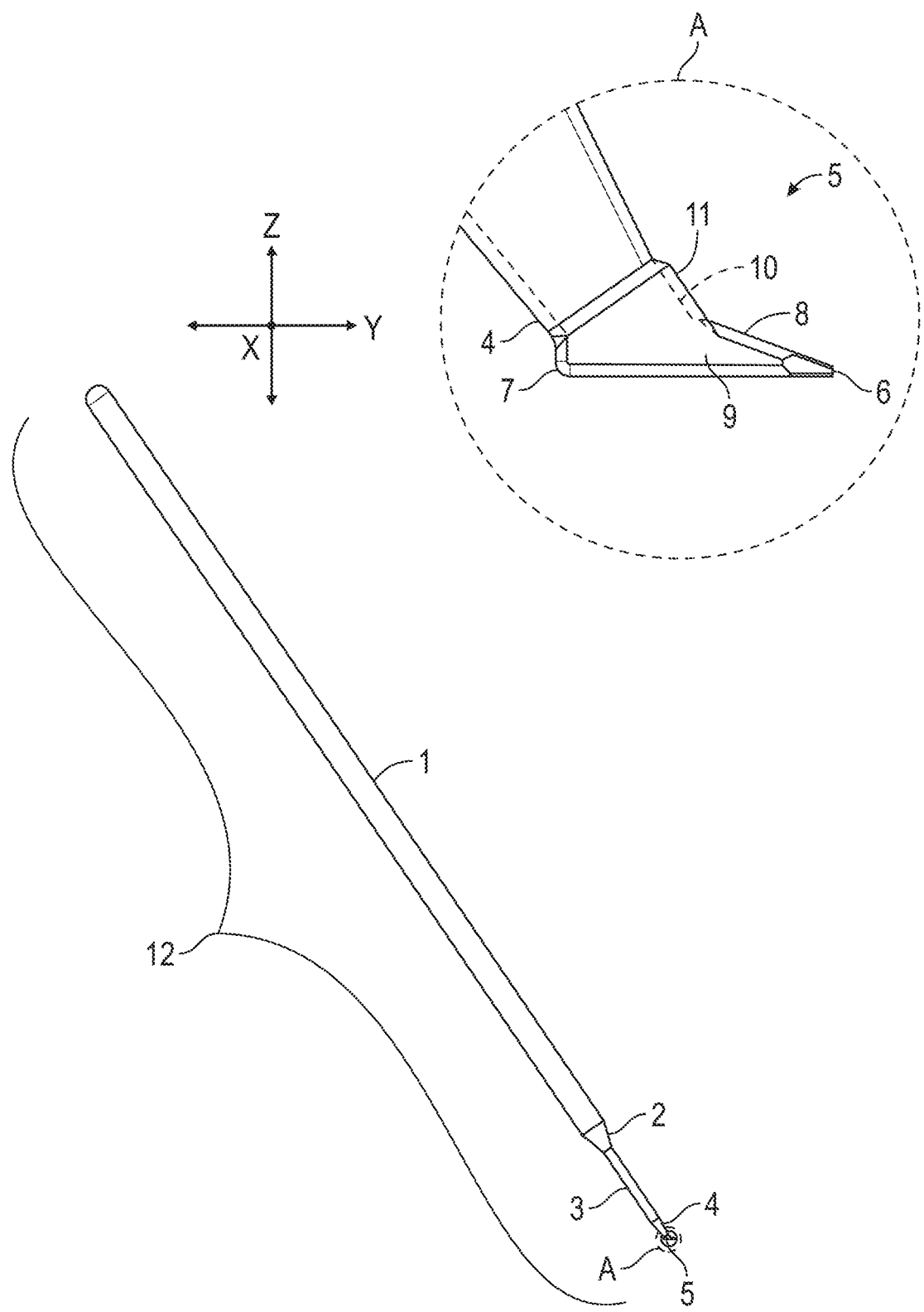
FIG. 1 shows an angled, side view of one embodiment of the device with an enlarged detailed view of the operative end of the device with the beveled platform.

LIST OF REFERENCE NUMERALS 1 handle
2 first interface
3 tool shaft
4 second interface
5 platform
6 insertion tip
7 second end/back of the beveled platform
8 first side
9 second side
10 first blade
11 second blade
12 device
13 second platform
14 third blade
15 fourth blade
16 barrel of the device
17 alligator clip
18 first alligator clip blade
19 second alligator clip blade
20 wire element
21 axial extension
22 internal lumen/collector channel
23 through-hole
24 fiber optic
25 ultrasonic emitter
26 grasping feature
27 sleeve or cap
28 sleeve or cap actuator switch
29 curved platform
30 first upper blade
31 second upper blade
32 handle trigger
33 blade heating element
34 lancet type/hollow/wire
35 double sided/bi-directional device
36 overhang
37 no beveled platform, angled blades
38 wedge
39 slidable punch

DETAILED DESCRIPTION OF THE INVENTION

The present invention relates to an ophthalmic knife and methods of its use for treatment of various conditions including eye diseases, such as glaucoma, using minimally invasive surgical techniques. An ophthalmic knife can be used for cutting the tissues within the eye, for example, a trabecular meshwork (TM). This invention also relates to surgical medicinal intervention. For example, the present invention relates to a microsurgical device and methods of its use for treatment of various medical conditions including but not limited to eye diseases, such as glaucoma, using minimally invasive surgical techniques.

I. Conventional Treatments for Ocular Diseases

A. Glaucoma

Glaucoma is believed to be one of the leading causes of blindness worldwide [1]. It has been reported that a modifiable disease risk factor is intraocular pressure (TOP). Conventional treatment has centered on lowering IOP pharmaceutically with hypotensive medications or surgically through the use of lasers or incisional procedures. The main area of obstruction to aqueous outflow, with subsequent dysregulation of IOP, is thought to be located at the juxtacanalicular trabecular meshwork (TM) and distal outflow structures [2-4]. Performing a goniotomy or trabeculotomy in adults with glaucoma has not been associated with great success in lowering IOP [5, 6]. In contrast, these procedures have been reported to be more successful in congenital glaucoma, where a membrane covering the TM is thought to be a major factor in impedance of aqueous outflow [7]. More recently, there have been attempts to use novel ab intern trabeculectomy procedures to remove TM in adult patients and results have been mixed [8-10].

One reason for poor long-term outcomes with this approach in adults might be related to incomplete removal of TM and membrane formation across the remaining TM leaflets with subsequent elevation in IOP [11]. It is unclear how a more complete removal of TM tissue might compare to procedures that simply incise TM, such as an MVR blade goniotomy, or procedures that cauterize TM with tissue removal, such as Trabectome® (Neomedix, Tustin, Calif., USA). The dual-blade device is specifically designed to conform to the drainage angle anatomy of the human eye. While not limiting the current invention, the device is meant to perform an ab intern trabeculectomy by engaging TM and cutting the target tissue while minimizing leaflets left in place and damage to adjacent tissues. The device was designed and manufactured at the University of Colorado Eye Center (U.S. Provisional Patent Application No. 61/637, 611) [12]. Tissue effects from the novel device are compared to those from a goniotomy using a microvitreoretinal (MVR) blade (BD, Franklin Lakes, N.J., USA) and cautery of TM with the Trabectome® device. Human eye perfusion studies were also completed to assess the IOP-lowering efficacy of each approach.

Recently, there has been a growing trend toward innovations in minimally invasive glaucoma surgery (MIGS). The risks and imperfections of guarded filtration surgery and tube shunt procedures have driven this paradigm shift despite the proven long-term efficacy of these incisional procedures. Drawbacks of traditional incisional procedures include unpredictable IOP-lowering results, prolonged visual recovery, long-term risk of infection and vision loss, frequency of follow-up visits, and long-term failure rate [13]. Procedures such as endoscopic cyclophotocoagulation, ab intern trabeculectomy with Trabectome®, and canaloplasty with the iScience illuminated catheter (iScience, Menlo Park, Calif., USA) were all introduced to address limitations of full-thickness surgery, most notably to eliminate the presence of a filtering bleb. However, a major drawback of all of these procedures is the additional equipment cost required and, in some cases, a steep learning curve. The added equipment cost in particular presents a significant hurdle to providers, hospitals, and surgery centers that may require several procedures to recoup the initial investment. Providers and patients may also face opposition from insurance companies regarding coverage of a novel procedure lacking longterm efficacy data. The requirement for additional equipment also limits patient access to these procedures in underserved areas of the world.

B. Goniotomy

A goniotomy is generally referred to as a surgical procedure primarily used to treat congenital glaucoma. It can be caused by a developmental arrest of some of the structures within the anterior (front) segment of the eye. These structures include the iris and the ciliary body, which produces the aqueous fluid needed to maintain the integrity of the eye. These structures do not develop normally in the eyes of patients with isolated congenital glaucoma. Instead, they overlap and block the trabecular meshwork, which is the primary drainage system for the aqueous fluid. Because of this blockage, the trabecular meshwork itself becomes thicker and the drainage holes within the meshwork are narrowed. These changes lead to an excess of fluid in the eye, which can cause pressure that can damage the internal structures of the eye and cause glaucoma.

In general, congenital glaucoma is caused by a decrease in or even a complete obstruction of the outflow of intraocular fluid. The ocular syndromes and anomalies that predispose a child to congenital glaucoma include the following: Reiger's anomaly; Peter's anomaly; Axenfeld's syndrome; and Axenfeld-Rieger's syndrome. Systemic disorders that affect the eyes in ways that may lead to glaucoma include Marfan's syndrome; rubella (German measles); and the phacomatoses, which include neurofibromatosis and Sturge-Weber syndrome. Since these disorders affect the entire body as well as the eyes, the child's pediatrician or family doctor will help to diagnose and treat these diseases.

One purpose of a goniotomy is to clear the obstruction to aqueous outflow from the eye, which in turn lowers the intraocular pressure (IOP). Although it is not necessary to understand the mechanism of an invention, it is believed that lowering the IOP helps to stabilize the enlargement of the cornea and the distension and stretching of the eye that often occur in congenital glaucoma. The size of the eye, however, may not return to normal. Most importantly, once the aqueous outflow improves, damage to the optic nerve is halted or reversed. The patient's visual acuity may improve after surgery.

Before the surgeon begins the procedure, the patient may be given miotics, which are drugs that cause the pupil to contract. The partial closure may improve the surgeon's view of and access to the trabecular meshwork; it may also protects the lens of the eye from trauma during surgery. Other drugs may be administered to lower the intraocular pressure. Goniotomy procedures may be done without use of miotics. In one embodiment, the current invention may be used in the setting of a dilated (non-miotic) pupil, as can devices described as prior art.

Once the necessary drugs have been given and the patient is anesthetized, the surgeon may use forceps or sutures to stabilize the eye in the correct position. The patient's head may be rotated away from the surgeon so that the interior structures of the eye are more easily seen. Next, with either a knife-needle or a goniotomy knife, the surgeon punctures the cornea while looking at the interior of the eye through a microscope or a loupe. An assistant may use a syringe to introduce fluid into the eye's anterior chamber through a viscoelastic tube as the surgeon performs the goniotomy.

A gonioscopy lens may be then placed on the eye. As the eye is rotated by an assistant, the surgeon sweeps the knife blade or needle through 90-120 degrees of arc in the eye, making incisions in the anterior trabecular meshwork, avoiding the posterior part of the trabecular meshwork in order to decrease the risk of damage to the iris and lens. Endoscopic visualization may also be used to guide cutting. In one embodiment, the device of the current invention may be place at the end of an endoscope, precluding the need for a gonio lens during treatment. Once the knife and tubing are removed, saline solution may be introduced through the hole to maintain the integrity of the eye and the hole is closed with sutures. The surgeon then applies antibiotics and corticosteroids to the eye to prevent infection and reduce inflammation. The head may be then rotated away from the incision site so that blood cannot accumulate. The second eye may be operated on at the same time. If the procedure needs to be repeated, another area of the eye may be treated.

Previous devices have been described in Sorensen et al., "Tubular Cutter Device and Methods For Cutting and Removing Strips of Tissue from the Body of a Patient," U.S. Pat. No. 7,959,641 (Issued Jun. 14, 2011; [14]) Also see International Publication No. WO 2004/110501 [15] and United States Publication No. US 2007/0276420 related parts [16]). This reference discloses a device for cutting a strip of tissue with a width of about 50-200 μm from the trabecular meshwork. The device has a first and second cutting edge formed on the distal end of the cutting tube. The tip can be blunt and in some applications is configured and used to facilitate the insertion of the device into its intended location i.e. Schlemm's canal. Further, one or more bends or curves may be optionally formed to facilitate its use. The tip of the device may be advanced through the trabecular meshwork and into the Schlemm's canal thereby causing the cutting edges to cut a strip of the trabecular meshwork, thereby creating an opening for drainage of aqueous humor. While this reference teaches a cutting blade with dual cutting sides and a tip for placement into Schlemm's canal for removal of trabecular meshwork with optional bends/curvatures it does not specifically mention use of a 0.3 mm blade width.

Another device is described in Huculak, "Small Gauge Mechanical Tissue Cutter/Aspirator Probe for Glaucoma Surgery," United States Patent Publication No. US 2009/0287233 [17]. This reference discloses use of a small gauge mechanical tissue cutter/aspirator probe to remove trabecular meshwork. The probe can be guided into Schlemm's canal and moved in a forward motion following the curvature of the trabecular meshwork. The motion causes the trabecular meshwork to be fed into the cutting port of the cutter, thereby cutting and removing the trabecular meshwork that blocks the outflow of aqueous humor. Due to the size of Schlemm's canal, it is preferable to have the distal end of the outer cannula measure about 0.25 to 0.36 mm diameter. The cannula can be tapered so its distal end measures about 0.25 to 0.36 mm (Schlemm's canal is about 0.3 mm). Further, the leading edge can be curved to enhance its ability to pierce the trabecular meshwork. While the reference teaches use of a small gauge cutter with a diameter of about 0.25 to 0.36 mm with a sharp or blunt leading edge for piercing the trabecular meshwork and entry into Schlemm's canal with a cutting port to cut the trabecular meshwork it does not per se teach a dual sharp edge cutting blade.

Another device is described in Baerveldt et al., "Minimally Invasive Glaucoma Surgical Instrument and Method," United States Patent Publication No. US 2011/0077626 [18] (Also see U.S. Pat. No. 7,785,321 [19] and U.S. Pat. No. 6,979,328 [20]; and United States Patent Publication No. US 2006/0106370 [21] and US 2002/0111608 [22] selected parts). This reference discloses use of a cutting probe to cut and remove trabecular meshwork. The probe comprises a tip that is approximately 25 gauge (about 0.5 mm). The tip further comprises a footplate that serves as a guide into Schlemm's canal. The sharpened end of the footplate is used to pierce the trabecular meshwork. The trabecular meshwork is cut using a rotatable blade or cut in a guillotine fashion. While the reference discloses use of a cutting probe with a tip approximately 25 gauge including a footplate for piercing the trabecular meshwork and targeting Schlemm's canal it does not per se mention use of a dual sharp edge cutting blade sized for navigating Schlemm's canal (0.3 mm). Another device is described in Huculak, "Small Gauge Mechanical Tissue Cutter/Aspirator Probe for Glaucoma Surgery," International Publication No. WO 2009/140185 [23] (Also see European Patent No. EP 2303203 [24] selected parts). This reference discloses use of a small gauge mechanical tissue cutter/aspirator probe to remove trabecular meshwork. The probe consists of an outer cannula and an inner cannula. The inner cannula's distal end is configured to cut tissue when it enters port 310. The inner cannula is moved up and down to cut tissue. The outer cannula includes a retractable pick that has a sharp end for piercing the trabecular meshwork. Due to the size of Schlemm's canal, it is preferable to have the distal end of the outer cannula measure about 0.25 to 0.36 mm in diameter. The cannula can be tapered so its distal end measures about 0.25 to 0.36 mm (Schlemm's canal is about 0.3 mm). While the reference discloses use of a probe sized between 0.25 and 0.36 mm for piercing the trabecular meshwork and placement into the Schlemm's canal, it does not mention use of a dual sharp edge cutting blade with a curvature for navigating Schlemm's canal.

Another device is described in Bergheim, O. B. and Gharib, M. "Apparatus and Method for Treating Glaucoma," WIPO Patent WO/2001/078631 Application PCT/US2001/007398, filed Mar. 8, 2001. (Published Oct. 25, 2001) [25]. This reference discloses use of a cutting member positioned at the distal end of a tube consisting of a knife, a pointed guide member, and a sharpened distal end of said tube. The cutting member is configured to form an opening in the trabecular meshwork for placement of a seton into Schlemm's canal. The knife includes a microknife sized within the range of 20 to 40 gauge preferably 30 (0.3 mm) gauge. While the reference discloses use of a cutting member sized from 20 to 40 gauge for cutting the trabecular meshwork and delivery of a seton to Schlemm's canal it does not mention use of a dual sharp edge cutting blade with a curvature for navigating Schlemm's canal.

Another device is described in Skjaerpe, Finn, "Microsurgical Instrument," U.S. Pat. No. 4,501,274 [26] (Issued Feb. 26, 1985; also see European Patent No. EP 0073803 [27] selected parts). This reference discloses a microsurgical probe with a cutting member comprised of two knife blades protruding in different directions from the probe each with at least one sharp cutting edge. The cutting member has a double-cutting knife, where the two cutting edges are angularly separated such that they create a V-fount adapted to the local anatomical features of the eye at the Schlemm's canal and the trabecular meshwork. The probe diameter is approximately 0.25 mm and the width of the knives is 0.3 to 0.5 mm. The knife blades also include a cutting edge on both sides so the probe can be pulled in both directions through the Canal of Schlemm. While the reference discloses a dual-knife with at least one sharp cutting edge for cutting the trabecular meshwork and the inner wall of Schlemm's canal it does not per se mention a curvature for navigating Schlemm's canal.

Another device is described in Conston et al., "Ophthalmic Microsurgical System," United States Patent Publication No. US 2006/0149194 [28] (Also see International Publication No. WO 2003/045290 [29], European Patent No. EP 1455698 [30] and Korean Patent No. KR 1020040058309 [31] selected parts). This reference discloses a microsurgical system with an outer microcannula sheath that includes an inner member that is sized to adapt to the Schlemm's canal that is about 50 to 200 microns in diameter. The inner member is in the range of 50-240 microns in outer diameter in order to fit within the outer cannula, which is 50-250 microns in inner diameter. The outer microcannula and inner member each are adaptable to the curvature of Schlemm's canal and the inner member optionally includes a cutting tool at the distal end with a diamond or sapphire tip or blade or similar element. While the reference discloses a micro sized probe for cutting trabecular meshwork and targeting Schlemm's canal it does not per se mention use of a dual sharp edge cutting blade for piercing the trabecular meshwork and targeting Schlemm's canal.

Another device is described in Conston et al., "Ophthalmic Microsurgical Instruments," United States Patent Publication No. US 2007/0073275 [32] (Also see International Publication No. WO 2004/093761 [33] and European Patent No. EP 1615604 [34] selected parts). This reference discloses a microsurgical instrument that can be directly inserted into Schlemm's canal to allow controlled treatment or removal of adjacent tissues such as TM. The instruments comprise an outer sheath microcannula and an inner member where the distal end of the instruments can be curved to approximate the curvature of Schlemm's canal. The instruments include a cutting means to excise targeted tissue. The microcannula is sized to accommodate the Schlemm's canal (approximately 200 microns in diameter) approximately ranging from 100 to 350 microns outer diameter. The distal tip of an inner member can be beveled or sharpened to provide a cutting action. While the reference discloses a micro sized probe for cutting trabecular meshwork and targeting Schlemm's canal it does not per se mention use of a dual sharp edge cutting blade for piercing the trabecular meshwork and targeting Schlemm's canal.

Another device is described in Huculak, "Pulsed Electric Field Probe for Glaucoma Surgery," United States Patent Publication No. US 2011/0230877 [35]. This reference discloses use of a small gauge pulsed electric field probe for removal of trabecular meshwork. The distal end of the probe includes a pick adapted to fit into Schlemm's canal so the electric pulsed field can be used to dissociate and remove the trabecular meshwork. The pick has a sharp end so it can pierce the trabecular meshwork and so the pick can be placed into the Schlemm's canal. The pick is retractable. The probe has a diameter between 0.25 and 0.36 mm. While the reference discloses use of a probe sized between 0.25 and 0.36 mm for piercing the trabecular meshwork and placement into the Schlemm's canal, it does not mention use of a dual sharp edge cutting blade with a curvature for navigating Schlemm's canal.

Another device is described in Pantcheva, M. B. and Kahook, M. Y. (2010) Ab Interno Trabeculectomy, Middle East Afr. J. Ophthalmol. 17(4), 287-289 [10]. This reference is a review of the Trabectome® device that is used in this general field.

Another device known in the art that has been used for ab intern trabeculectomy is known as the "gonioscraper," as described by Jacobi and associates [36]. This device consisted of a handle and curette tip and was used to remove TM by scraping the curette within the Schlemm's canal. The curette tip is in line with the handle and does not conform to the geometry of the drainage angle and adjacent structures. After promising preclinical experiments, a nonrandomized clinical trial of 25 eyes was completed [37]. Preoperative IOP was 34.7±7.1 mm Hg on 2.2+0.56 medications and mean follow-up time was 32 months. Based on the success criteria of postoperative IOP of 19 mm Hg or less with 1 pressure-reducing agent, 15 eyes (60%) were successful. Nonetheless, complications developed in some patients including localized Descemet membrane detachments and/or anterior chamber bleeding. Histologic analysis of banked human eyes treated with the curettage showed successful removal of TM tissue, but with damage to the septa and endothelium of the external and posterior wall of the Schlemm's canal [36]. In the data presented herein, similar damage to adjacent sclera was also observed when using the MVR blade, but was notably absent with use of one embodiment of a dual-blade device as contemplated by the present invention.

There have been reports of both success and failure with the Trabectome® device over the past few years [8-11, 38]. In a recent retrospective study of Trabectome® versus ab externo trabeculectomy, Jea and associates found poor success rates in eyes treated with Trabectome® at 2 years [8]. Of the 115 eyes treated with Trabectome®, only 22.4% achieved success with failure defined as IOP>21 mm Hg or <20% reduction in IOP. It is conceivable that, after initial opening of the canal with TM removal, the residual leaflets occlude the Schlemm's canal and/or the more distal collector channels, leading to failure of the intervention. This mechanism of failure after Trabectome® treatment would be overcome by the dual-blade device, as a more complete removal of TM tissue is produced without residual leaflets.

A modified dual blade device geometry was designed to minimize any impact to adjacent tissues such as Descemet membrane by leveraging specific angles between the handle and the distal blade as well as use of specific angles between the cutting blade and the adjacent cutting tip. Kahook M., WO 2013/163034 [39] (herein incorporated by reference). Several practical advantages of a dual blade device for use in ab intern trabeculectomy were reported. First, a dual blade device may be reusable and can be added to a standard cataract surgical tray. Second, the lack of moving parts or the need for coupled irrigation or a separate power source allows for inexpensive manufacturing and rapid acquisition of surgical expertise. This would permit easy, economical access to a new technique, especially in underserved locations around the world. For comparison, a conventional Trabectome® device requires a substantial initial investment for the irrigation/aspiration unit and generator in addition to the cost of one-time-use items such as the hand piece and tubing. The simple design and material requirements of dual-blade device embodiments would be more economical. Finally, in contrast to other techniques for TM removal, embodiments of dual-blade device designs conform to the Schlemm's canal anatomy, minimizes damage to adjacent tissues, and provides excellent control over excised tissue. In conclusion, the conventional dual-blade device may perform ab interno trabeculectomy with or without concomitant cataract extraction.

II. Ophthalmic Knives

The following detailed description, and the drawings to which it refers, are provided for the purpose of describing and illustrating certain preferred embodiments or examples of the invention only, and no attempt has been made to exhaustively describe all possible embodiments or examples of the invention. Thus, the following detailed description and the accompanying drawings shall not be construed to limit, in any way, the scope of the claims recited in this patent application and any patent(s) issuing there from.

In one embodiment, the present invention contemplates an ophthalmic knife for cutting ocular tissue (e.g., for example, trabecular meshwork (TM)). In particular, the knife may have a device tip providing entry into the Schlemm's canal via its size (i.e., for example, between approximately 0.3-0.2 mm width) and a configuration where the entry blade tip curves up providing a ramp-like action for cutting tissue (e.g., for example, trabecular meshwork tissue).

Specific advantages of some embodiments described herein as compared to other conventional devices include but are not limited to:

1. No mechanically moving parts
2. No cautery or burning of tissue
3. A multi-blade configuration can be in place on the sides of the device that cut the TM in a precise fashion leaving little TM behind (current devices leave considerable residual TM leaflets behind that then scars over)
4. The entry into Schlemm's canal is done with use of the blade tip. Other similar devices use a non-blade footplate to enter Schlemm's canal.
5. The dimensions of these devices allow for a complete cutting and fit in Schlemm's canal with precision.
6. A tip of the blade may ramp up to the multiple side blades forming a surface that presents the TM to the blades, which then allows for more precise cutting.
7. A device distal end is a right triangle that follows the $a^2+b^2=c^2$.
8. The distal end ramps up from the piercing blade towards to parallel blades that are positioned above the level of the TM.
9. The ramp causes the TM to elevate away from canal of schlemm as the device is advanced thus lifting the TM above the usual position of the inner wall of the canal of Schlemm.
10. Once the TM is elevated and the device is advanced, the TM presents to the parallel blades resulting in a clean cut of the tissue.
11. The stretch of the tissue away from the natural position of the inner wall of the canal of schlemm is a key step for success.
12. The piercing tip blade is not continuous with the blades on the top of the ramp (i.e., there is no sharp part that is continuous from the tip all the way to the blades that cut the TM). The area of the ramp is generally devoid of a cutting edge.

13. In one embodiment, the device has a flat bottom which results in the bulk of the bottom of the device not touching the outer wall of Schlemm's canal once the device is placed flush with heel down (the curve of canal of Schlemm results in this (so the bottom of the footplate is cupped by canal of schlemm). This means less contact and friction with the footplate of the current invention as it is advanced.

14. All cutting of tissue (except for the initial piercing with the blade tip) is done away from (elevated towards the anterior chamber) canal of Schlemm.

A. An Ophthalmic Knife Platform

In some embodiments, the present invention contemplates an ophthalmic knife comprising a platform. In some embodiments, the platform comprises a ramp, thereby forming a beveled, or wedge shape 38. In some embodiments, the platform is attached to lateral blades, preferably on the lateral sides of the platform, see FIG. 1.

Figure 2:
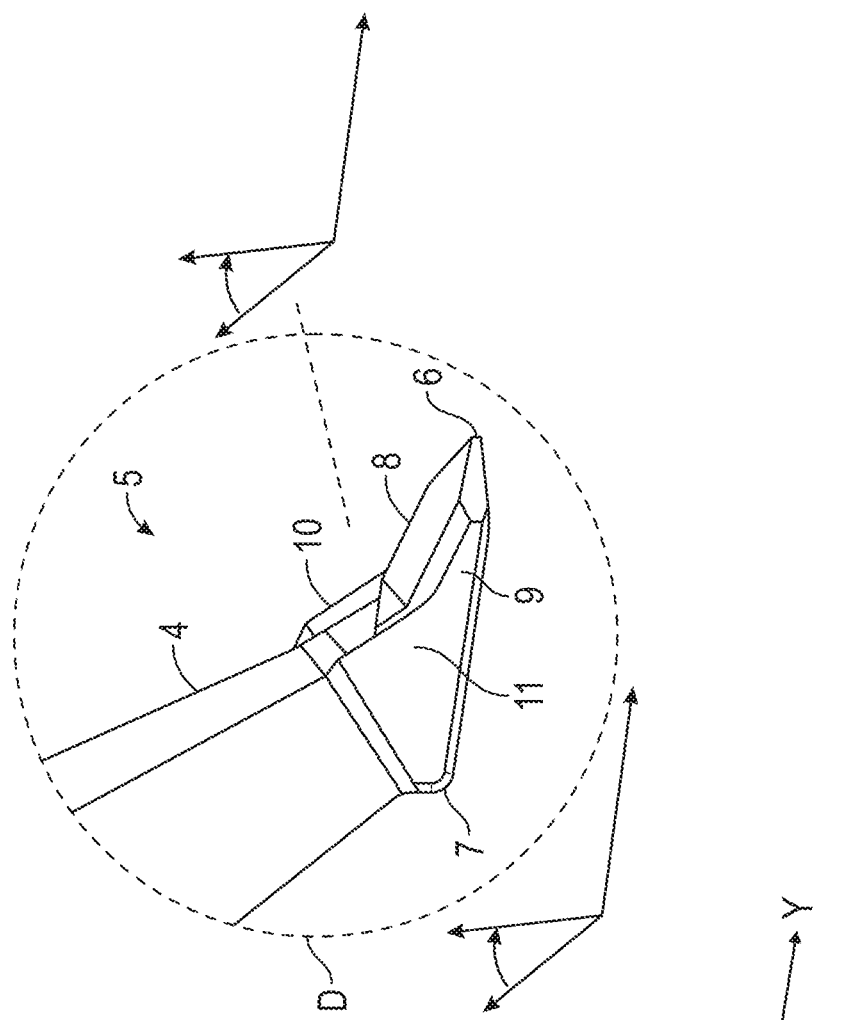
FIG. 2 shows an angled, side view of one embodiment of the device with an enlarged detailed view of the operative end of the device with the beveled platform 5. The shaded aspect provided a view of the dimensions of the beveled platform. The angle of tool shaft 3 attachment and of first and second blade attachment relative to the beveled platform 5 are indicated.

In one embodiment, a first lateral blade 10 and a second lateral blade 11 are in a perpendicular alignment to the bottom of the beveled platform 5. In one embodiment, the invention relates to a device 12 comprising a handle 1 and a beveled platform 5, wherein said platform 5 is set at a specific angle and orientation relative to said handle 1. In one embodiment, the invention relates to a device 12 comprising a handle 1 and a beveled platform 5, wherein said platform 5 freely rotates in at least two dimensions. In one embodiment, said handle 1 and beveled platform 5 are operably attached at an angle ranging between 90 and 120 degrees in the Y-Z axis. In one embodiment, said handle 1 and beveled platform 5 are operably attached at an angle ranging between 90 and 180 degrees in the X-Z axis. In one embodiment, said platform 5 freely rotates in an X-Y dimension relative to said handle 1. In one embodiment, said platform 5 remains at a fixed angle in the X-Y, X-Z, and Y-Z dimensions relative to said handle 1. In one embodiment, said platform 5 freely rotates in a positive Z dimension relative to said handle 1. In one embodiment, said beveled platform 5 comprises a first end/beveled platform tip/insertion blade tip 6 and a second end/back of the beveled platform 7, wherein said second end/back of the beveled platform 7 is between two and thirty times greater in thickness relative to said first end/beveled platform tip/insertion blade tip 6. In one embodiment, the dimensions of the beveled platforms 5 are dictated by the formula $A^2+B^2=C^2$, wherein A is the length of said beveled platform 5 from said insertion blade tip 6 to the back of the beveled platform 7, B is the height of the beveled platform 5 and C is the length of the ramp. In one embodiment, the height of said beveled platform 5 is not to exceed 0.5 millimeters. In one embodiment, the length of said beveled platform 5 from said insertion blade tip 6 to the back of the beveled platform 7, is not to exceed 1.0 millimeters. In one embodiment, said first end/beveled platform tip/insertion blade tip 6 comprises a fine surgical lancet. In one embodiment, said first end/beveled platform tip/insertion blade tip 6 comprises an angle of between 20 and 90 degrees. In one embodiment, said beveled platform 5 increases in thickness from a fine blade tip towards the second end/back of the beveled platforms 7 in the direction of the Y-axis. In one embodiment, said first end/beveled platform tip/insertion blade tip 6 comprises a pointed tip with fine edges of surgical sharpness. In one embodiment, said first end/beveled platform tip/insertion blade tip 6 comprises a lancet. In one embodiment, said beveled platform 5 further comprises a first blade 10 and a second blade 11. In one embodiment, said first blade 10 is attached to a first side 8 of said second end/back of the beveled platform 7. In one embodiment, said first blade 10 and beveled platform 5 are operably attached at an angle ranging between 90 and 180 degrees in the Y-Z axis. In one embodiment, said angle is preferably between 90 and 120 degrees in the Y-Z axis. In one embodiment, said second blade 11 and beveled platform 5 are operably attached at an angle ranging between 90 and 120 degrees in the Y-Z axis. In one embodiment, said first blade 10 and handle 1 are operably positioned at an angle ranging between 90 and 120 degrees in the Y-Z axis. In one embodiment, said second blade 11 and handle 1 are operably positioned at an angle ranging between 90 and 120 degrees in the Y-Z axis. In one embodiment, said second blade 11 is attached to a second side 9 of said second end/back of the beveled platform 7. FIG. 2. In one embodiment, wherein said anterior blade tip is a retractable blade tip.

Figure 3:
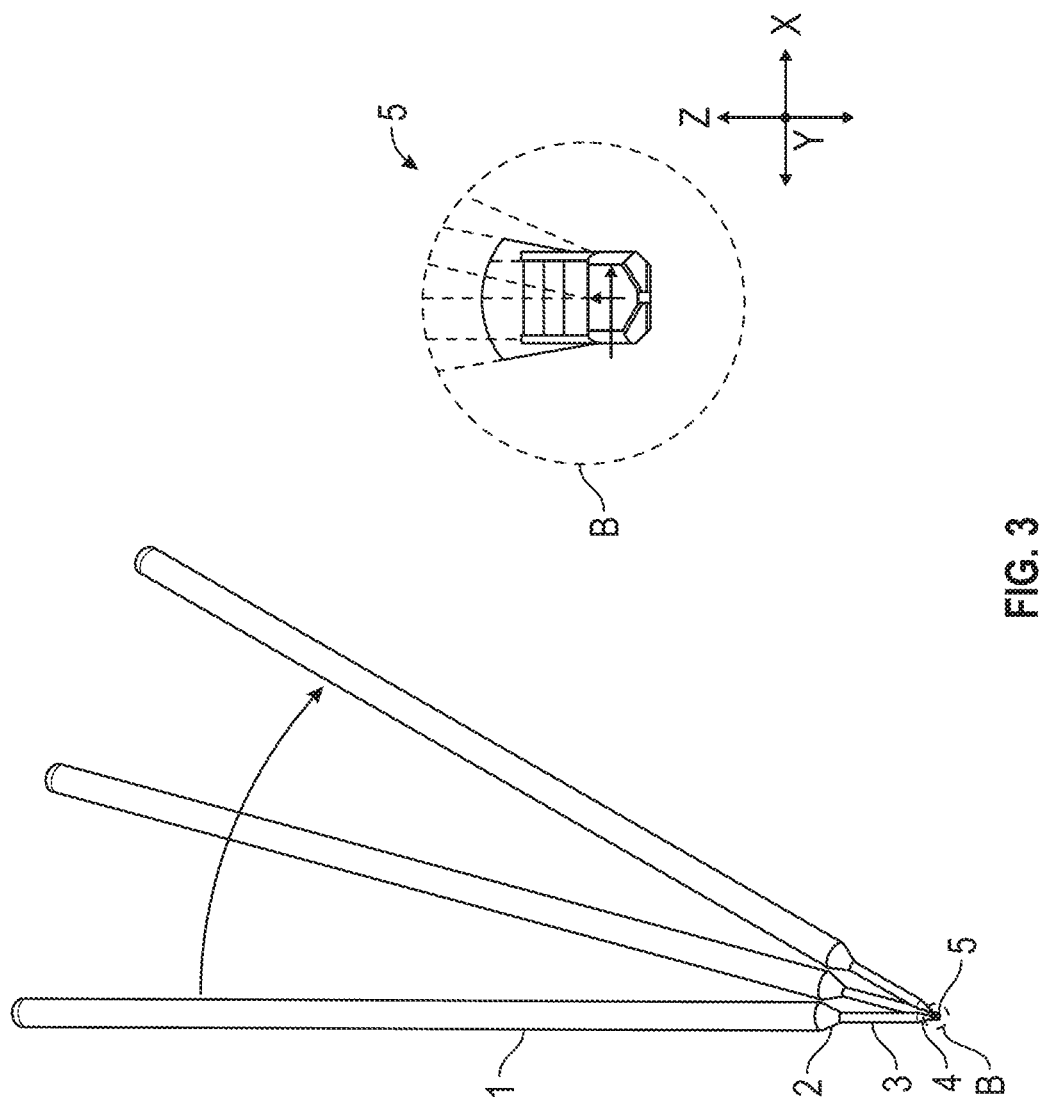
FIG. 3 shows a front face view of one embodiment of the device with an enlarged detailed view of the operative end of the device with the beveled platform 5. Shown are examples of the different angles of attachment of the handle 1 to the beveled platform 5 clockwise 0, 15, and 30 degrees relative to the Z-axis and X-axis. The increased platform thickness is also indicated as the platform extends from the insertion tip 6 towards the back of the platform 7 and from the first side (on the right) to the second side (on the left).

In one embodiment, said beveled platform 5 increases in thickness from said second side 9 towards the first side 8 in the direction of the X-axis. FIG. 3. In one embodiment, said beveled platform 5 increases in thickness from said second side 9 towards the first side 8 in the direction of the X-axis and said beveled platform 5 increases in thickness from a fine blade tip of the first end 6 towards the second end/back of the beveled platform 7 in the direction of the Y-axis.

In one embodiment, said beveled platform 5 increases in thickness from said first side 8 towards the second side 9 in the direction of the X-axis. In one embodiment, said beveled platform 5 increases in thickness from said first side 8 towards the second side 9 in the direction of the X-axis and said beveled platform 5 increases in thickness from a fine blade tip of the first end 6 towards the second end/back of the beveled platform 7 in the direction of the Y-axis. In one embodiment, said first blade 10 and said second blade 11 extend above the top surface of said second end/back of the beveled platform 7. In one embodiment, said first blade 10 and said second blade 11 are positioned at an angle between approximately 100 to 140 degrees relative to the top surface of said second end/back of the beveled platform 7. In one embodiment, said beveled platform 5 is approximately 0.3 millimeters wide. In one embodiment, said beveled platform 5 is approximately 0.2 millimeters wide. In a preferred embodiment, said beveled platform 5 is approximately 0.25 millimeters wide. In one embodiment, said beveled platform 5 is approximately 1.0 millimeters long. In one embodiment, said beveled platform 5 is approximately 0.4 millimeters high. In one embodiment, said highest point on the beveled platform 5 is the first and second blades. The device 12, may be provided as a pre-sterilized, single-use disposable probe or tip that is attachable to a standard surgical handpiece. In one embodiment, the device further comprises a fiber optic visualization system 24. In one embodiment, said shaft 3 further comprises a grasping feature 26. In one embodiment, said grasping feature 26 is selected from the group consisting of a tweezer element and a forcep element. In one embodiment, said grasping feature 26 comprises a sleeve 27 extending over said shaft, wherein said handle comprises a sleeve actuator switch.

B. A Dual Platform/Dual-Blade Ophthalmic Knife

In one embodiment, the present invention contemplates a dual platform/dual-blade ophthalmic knife comprising a handle 1 connected to a shaft 3, said shaft connected to a first platform and a second platform, said first platform comprising a first and second blade and a first anterior blade and said second platform comprising a third 14 and fourth 15 blade and a second anterior blade tip. In one embodiment, depicted in FIG. 4A, said device comprises two oppositely faced platforms with each platform each having at least two lateral blades and each having a blade tip. In another embodiment, depicted in FIG. 4B, the device comprises two roughly parallel platforms with each platform each having at least two lateral blades and each having a blade tip. In one embodiment, said first and second anterior blade tips are retractable blade tips. In another embodiment, the device comprises at least two offset platforms. In another embodiment, the device comprises at least two offset platforms each having at least two lateral blades and each having a blade tip C. A Quad-Blade Ophthalmic Knife In one embodiment, the present invention contemplates a quad-blade ophthalmic knife comprising a handle 1 connected to a shaft 3, said shaft connected to a platform comprising four cutting blades and an anterior blade tip, see FIG. 5. In one embodiment, the two upper (shaft) blades (30 and 31) positioned above the lower (platform) blades (10 and 11), the upper and lower blades being able to move up and down to cut TM between the upper and lower blades (like scissors on either side of the ramp). In one embodiment, the upper blades may be moved by triggering a mechanism 32, such as squeezing the handle 1 (like MST forceps).

D. An Ultrasonic Ophthalmic Knife

Figure 6:
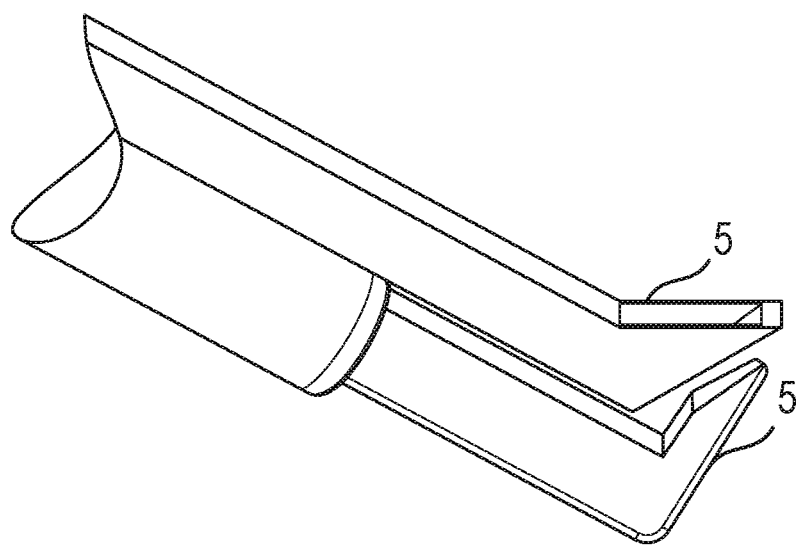
FIG. 6 depicts one embodiment of the ultrasonic ophthalmic knife.

In one embodiment, the present invention contemplates an ultrasonic ophthalmic knife comprises a handle 1, shaft 3, an anterior blade tip, and platform wherein the platform comprises an ultrasonic emitter 25. In one embodiment, said ultrasonic ophthalmic knife is shown in FIG. 6.

E. A Pincer Ophthalmic Knife

Figure 7:
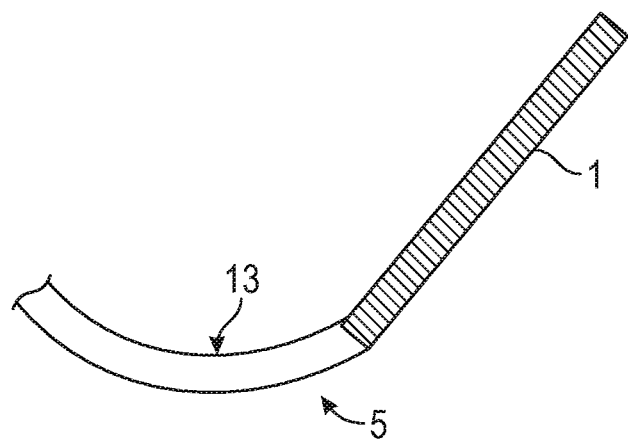
FIG. 7 presents an exemplary embodiment of a pincer ophthalmic knife comprising a lower platform comprising at least two blades and a hinged upper platform having a complementary surface to the lower platform. In one embodiment, said first platform is guided into the canal whilst the second platform is inside said handle, tool shaft, or barrel. In one embodiment, said first platform is advanced into TM and subsequently said second platform is then pushed down towards said first platform to capture TM between said first platform and second platform. In one embodiment, said platforms further comprise blades or recesses on both said first platforms and said second platform. In one embodiment, said platforms have curved surfaces. In one embodiment, said platforms have complementary surfaces. In one embodiment, said complementary surfaces articulate at a surface of articulation. In one embodiment, said surface of articulation is the edge of said blades. In one embodiment, said platforms marry to each other and amputate the strip of TM in one 8 mm strip.

In one embodiment, the present invention contemplates a pincer ophthalmic knife comprising a handle 1 connected to a shaft 3, said shaft connected to a lower platform and an upper platform. In one embodiment, said platforms are curved. In one embodiment, said first platform is guided into the canal whilst the second platform is inside said handle 1, tool shaft 3, or barrel 16. In one embodiment, said first platform is advanced into TM and subsequently said second platform is then pushed down towards said first platform to capture TM between said first platform and second platform. In one embodiment, said platforms further comprise blades or recesses on both said first platforms and said second platform. In one embodiment, said platforms have complementary surfaces. In one embodiment, said complementary surfaces articulate at a surface of articulation. In one embodiment, said surface of articulation is the edge of said blades. In one embodiment, said platforms marry to each other and amputate the strip of TM in one 8 mm strip. In one embodiment, said device is depicted in FIG. 7.

F. A Gripping Ophthalmic Knife

Figure 8:
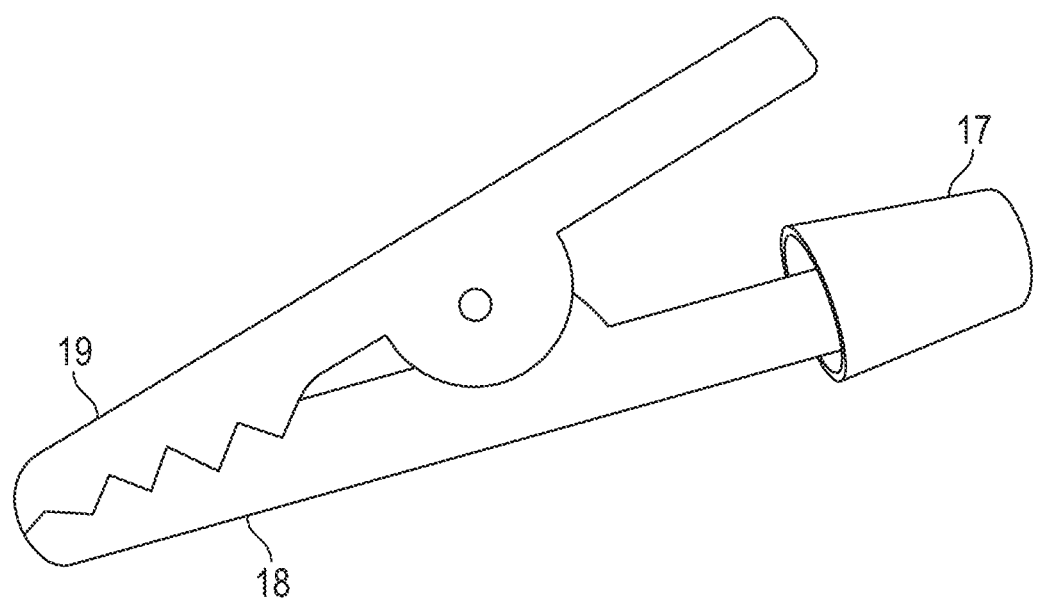
FIG. 8 presents an exemplary embodiment of a gripping ophthalmic knife comprises a shaft connected to one pair of serrated jaws (e.g., alligator clips).

In one embodiment, the present invention contemplates a gripping ophthalmic knife comprising a handle 1 connected to a shaft 3, said shaft comprises a lateral alligator clip 17, a platform connected to the shaft 3, said platform 5 comprising a first lateral blade 10 *a*, and an anterior blade tip 6. In one embodiment, said alligator clip 17 comprises a first 18 and second 19 alligator clip blades. In one embodiment, said alligator clip 17 comprises a clip with a spring that closes the articulating jaws. In one embodiment, said alligator clip comprises a clip with a spring that closes the serrated jaws. An example of an alligator clip (17) is shown in FIG. 8. In one embodiment, only the top jaw of said alligator clip moves up and down. In one embodiment, the bottom jaw of said alligator clip stays in the Schlemm's canal. In one embodiment, the elliptical motion of the top jaw of said alligator clip draws in the TM, cuts it, and then pushes it out from the back side.

G. A Lancet Ophthalmic Knife

Figure 9:
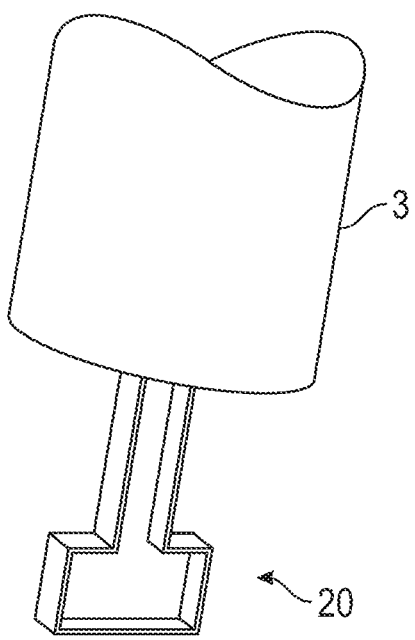
FIG. 9 presents an exemplary embodiment of a lancet ophthalmic knife comprising a wire element connected to a shaft.

In one embodiment, the present embodiment contemplates a lancet ophthalmic knife comprising a handle 1 connected to a shaft 3, said shaft connected to a wire element 20. In one embodiment, the shape of said wire element may retract into said shaft 3. In one embodiment, said wire element is rigid. In one embodiment, the shape of said wire element may be various, from having a tip to as simple as a square wire. In one embodiment, said wire element 20 has at least one sharp edge. In one embodiment, said wire element 20 has at least one dull edge. In one embodiment, said wire element 20 has a square shape, as depicted in FIG. 9. In one embodiment, said wire element 20 can be a triangle, square, rectangle, or an ellipse. In one embodiment, said wire element 20 is pushed into the TM. In doing so said wire element 20 stretches open the Schlemm's canal a bit. The wire element 20 is then advanced through the canal so that the sharp wire cuts the TM leaving a long trailing strip of TM.

H. An Axial Blade Ophthalmic Knife

Figure 10:
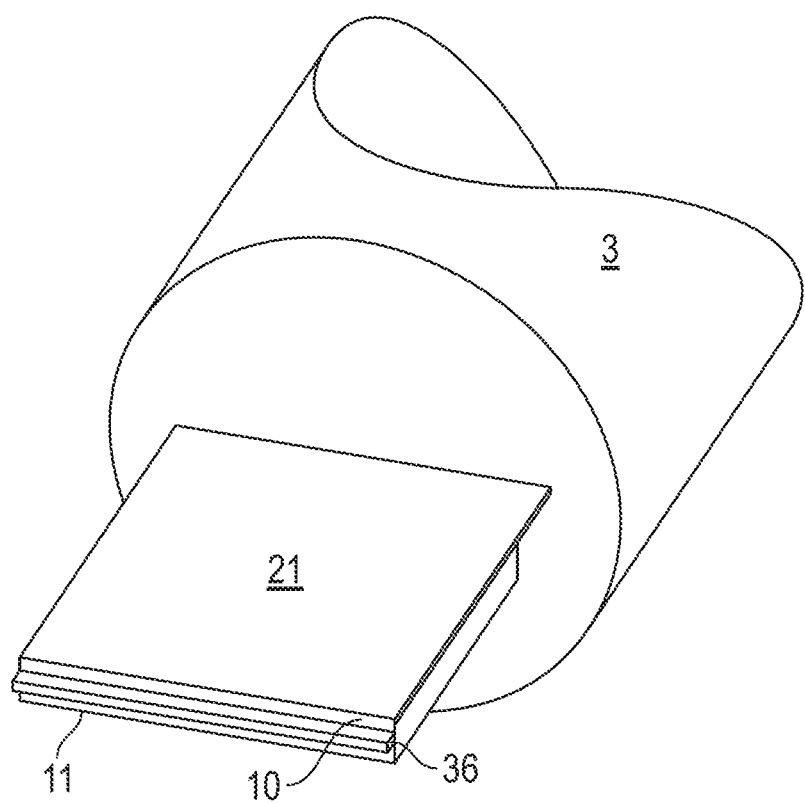
FIG. 10 presents an exemplary embodiment of an axial ophthalmic knife comprising at least two blades connected to a shaft.

In one embodiment, the present invention contemplates an axial blade ophthalmic knife comprising a handle 1 connected to a shaft 3, said shaft connected to a first and second blade. In one embodiment, said axial blade comprises an axial extension 21 comprising at least one distal blade. In one embodiment, said distal blade is affixed to said axial extension wherein the distance between said blade and the edge of said axial extension distal tip comprises an overhang 36. In one embodiment, said overhang 36 limits the depth of the cut. In one embodiment, depicted in FIG. 10, said device comprises two parallel blades (10 and 11) attached to said axial extension 21, wherein the space between the blades and the edge of said axial extension 21 comprises an overhang 36.

I. A V-Blade Ophthalmic Knife

Figure 11:
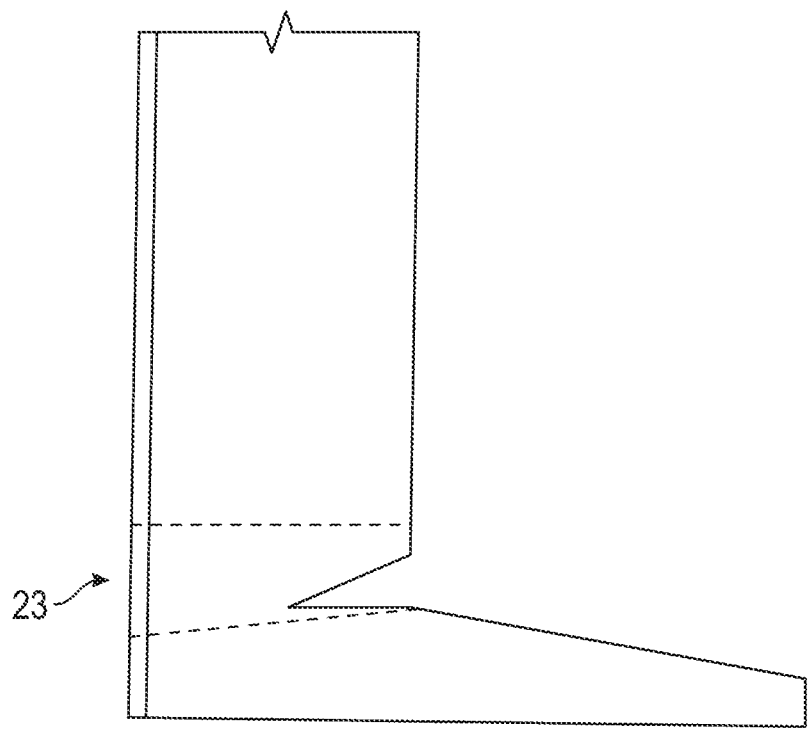
FIG. 11 presents an exemplary embodiment of a V-blade ophthalmic knife.
Figure 12:
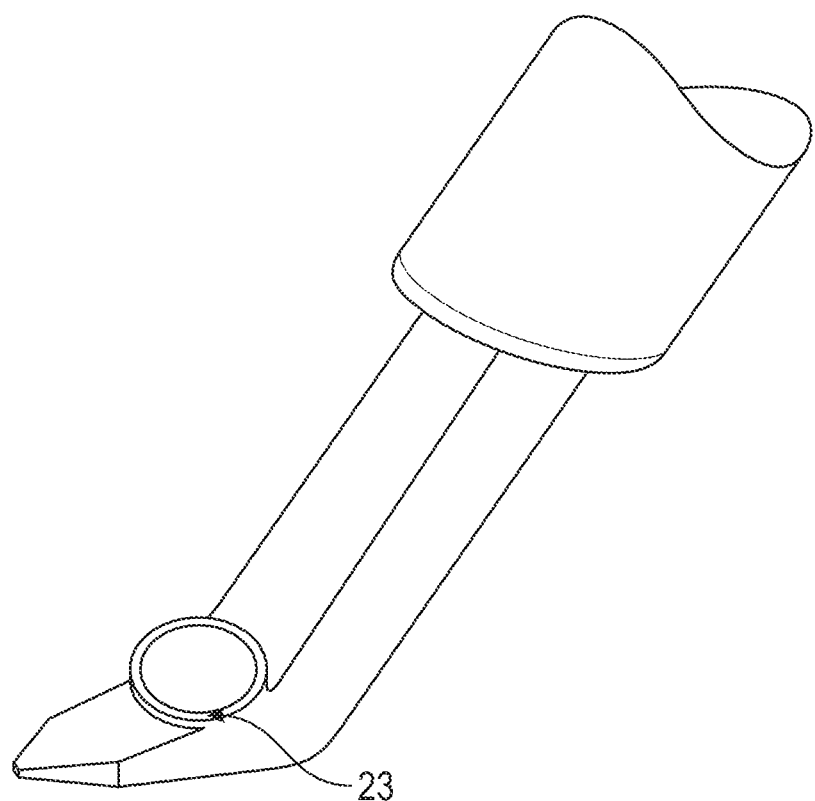
FIG. 12 presents an exemplary embodiment of an ophthalmic knife having a platform comprising a through-hole.
Figure 13:
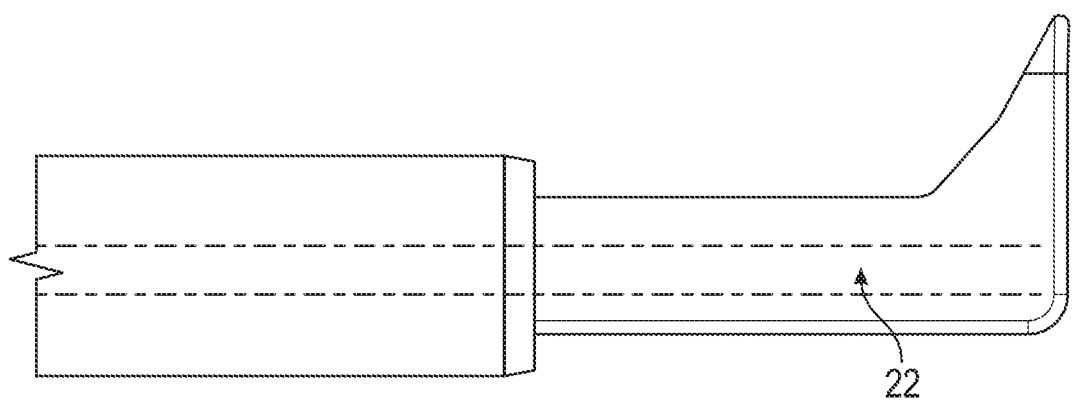
FIG. 13 presents an exemplary embodiment of an ophthalmic knife comprises at least one internal lumen.
Figure 14:
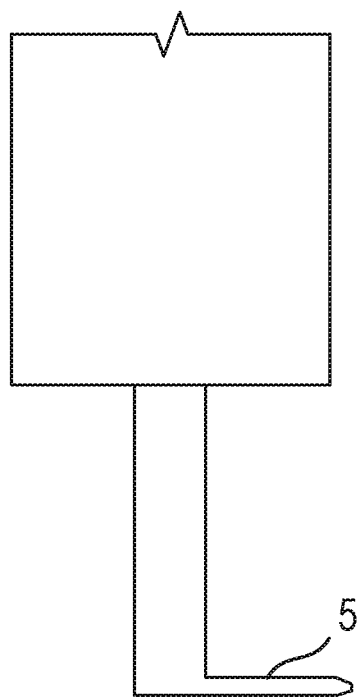
FIG. 14 presents an exemplary embodiment of an ophthalmic knife comprising a platform that lacks a ramp (or bevel).
Figure 15:
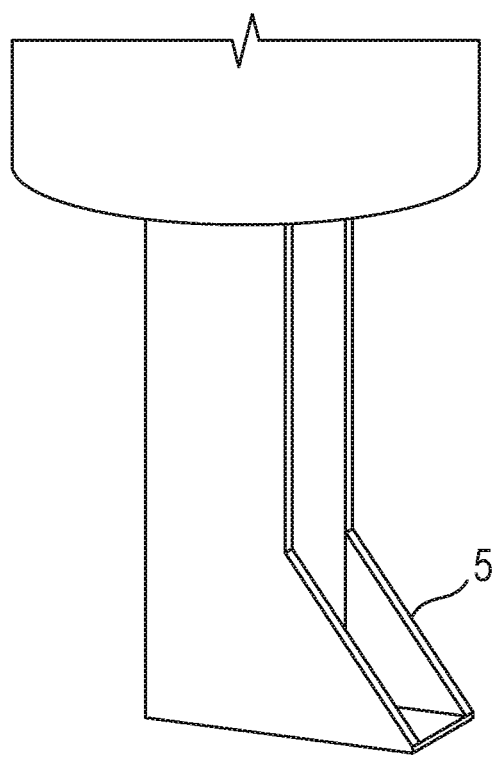
FIG. 15 presents an exemplary embodiment of an ophthalmic knife comprising a platform attached to two blades, wherein the blades extend from the posterior end to the distal anterior blade tip.

In one embodiment, the present invention contemplates a V-blade ophthalmic knife comprising a handle I connected to a shaft 3 comprising a first blade, said shaft connected to a platform, wherein the first blade overhangs said platform such that the first blade and said platform are connected at an angle. In one embodiment, the angle of attachment and overhand of said shaft 3 to said platform provides a surface for shearing tissue. In one embodiment, said knife further comprises a pass through window for cut tissue. FIG. 11 provides a side view of one embodiment of this device, wherein the dashed lines indicates one embodiment of the internal through-hole 23.

J. Ophthalmic Devices

Figure 16:
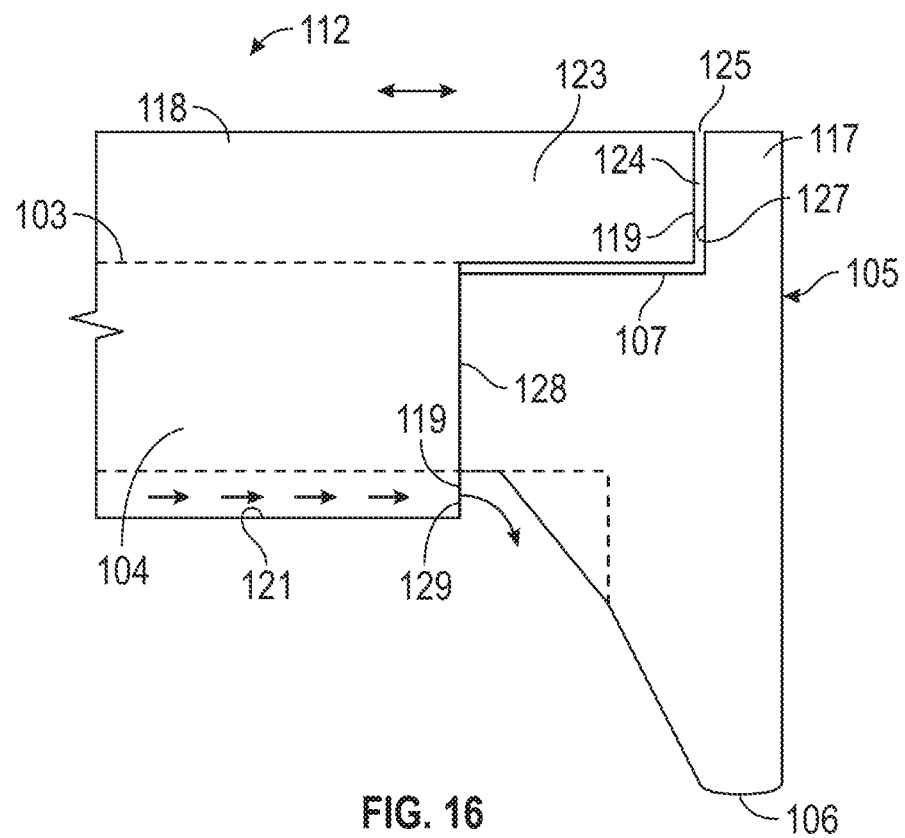
FIG. 16 shows a front view of a device according to embodiments of the present disclosure.

As shown in FIG. 16, a device 112 may have a platform 105 having an extension member 117. Platform 105 has a front tip 106 and a back end 107. Platform 105 may have similar features as platform 5, with the addition of the extension member 117. Device 112 may include a slidable sleeve 118 disposed over a shaft 104 and configured to slide back and forth over an external shaft surface 103 of the shaft 104 and at least a portion of the platform 105. The sleeve 118 may be sized and shaped to provide a fluid flow channel 119 between the shaft surface 103 and an inner sleeve surface 121. The fluid flow channel 119 may be configured to deliver a local balanced salt solution, a medication, viscoelastics (e.g. OVD) or therapeutic agents to the site or to wash away reflux of blood, for example.

The sleeve 118 may have a sleeve end 128 from which an engagement portion 123 may extend. The engagement portion may be sized and shaped to engage the extension member 117 when the sleeve 118 is slidably disposed in a closed position towards the extension member 117. The engagement portion 123 has a surface 124 configured to grasp tissue that has been cut or dissected by the platform 105. For example, the sleeve 118 may be positioned in a generally open position so that there is a gap 125 between the surface 124 and the extension member 117. The gap 125 may have a maximum width when the sleeve 118 is maximally retracted, where the width of the gap 125 lessens as the sleeve 118 moves to a fully engaged position against the extension member, whereupon the gap 125 may have little or no width.

The gap 125 may provide an outlet for fluid to be dispersed out from the fluid flow channel 119. Fluid may also be dispersed from an end portion 129 of the fluid flow channel 119. The fluid flow channel 119 may be configured to suction fluid back from the site. For example, fluid from the site (e.g., blood, excess irrigation fluid) may flow into the gap 125 and/or the end portion 129 and flow through the fluid flow channel 119 and exit a handle end of the device 112. As another example, the fluid channel 119 may be configured to deliver a fluid out the gap 125 and/or end portion 129 and returning fluid may move back up the device 112 through a lumen internal to the shaft 104 (not shown). In an aspect of the disclosure, a lumen may be disposed external to the shaft 104 and within the fluid flow channel 119.

The surface 124 may be provided as a grasping surface configured to engage tissue, thus allowing the sleeve 118 to grasp tissue between the surface 124 and the extension member 117. The tissue may then be removed by removing the device 112 from the site to dispose of the tissue or by using another device (e.g., phacoemulsification). In an aspect of the disclosure, the surface 124 may be provided as a forcing surface configured to force tissue down on to a cutting surface 127 of the extension member 117. Thus, the platform 105 may have multiple cutting portions.

Figure 21:
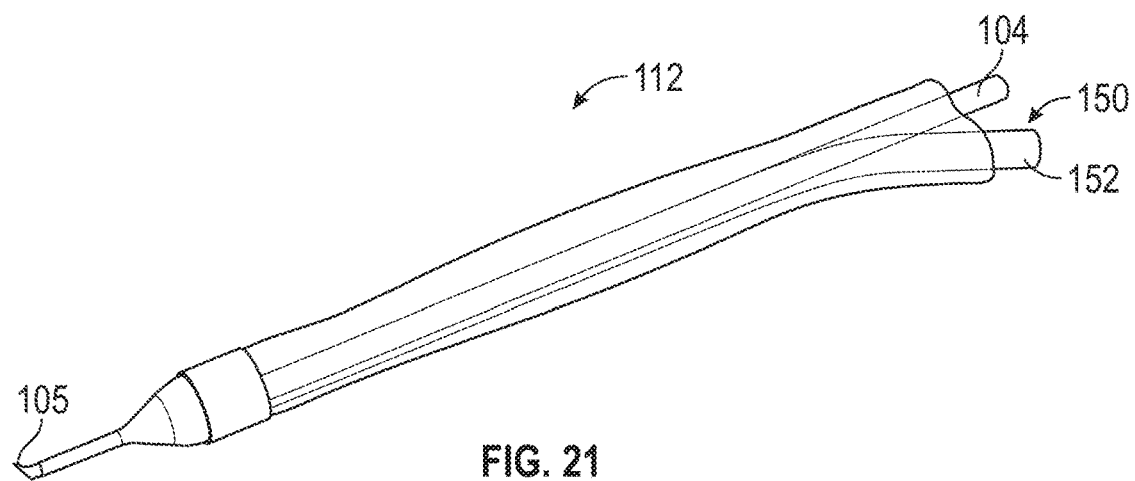
FIG. 21 shows a perspective view of a device with an activating handle according to embodiments of the present disclosure.

The sleeve 118 may be coupled to an engagement member of a handle, such as a squeeze handle 150 for example, as shown in FIG. 21. Thus, when an activation member (e.g., trigger) 152 of the handle 150 is squeezed, the sleeve 118 may be slidably moved towards the platform 105, providing for grasping and/or cutting tissue between the surface 124 and the extension member 117. Similarly, when the squeezing force on the handle 150 is removed (e.g., release trigger 152), the sleeve 118 may be slidably moved away from the platform 105, providing for a release of the tissue. In an aspect of the disclosure, the biasing force on the sleeve 118 may be reversed. For example, when the handle 150 is open (e.g., not squeezed), the sleeve 118 may be disposed so that the surface 124 engages the extension member 117 (e.g., the sleeve 118 is in the closed position), and when the handle 150 is squeezed, the sleeve 118 may be slidably moved away from the platform 105, opening a gap 125 so that tissue or an object may be engaged.

Figure 17:
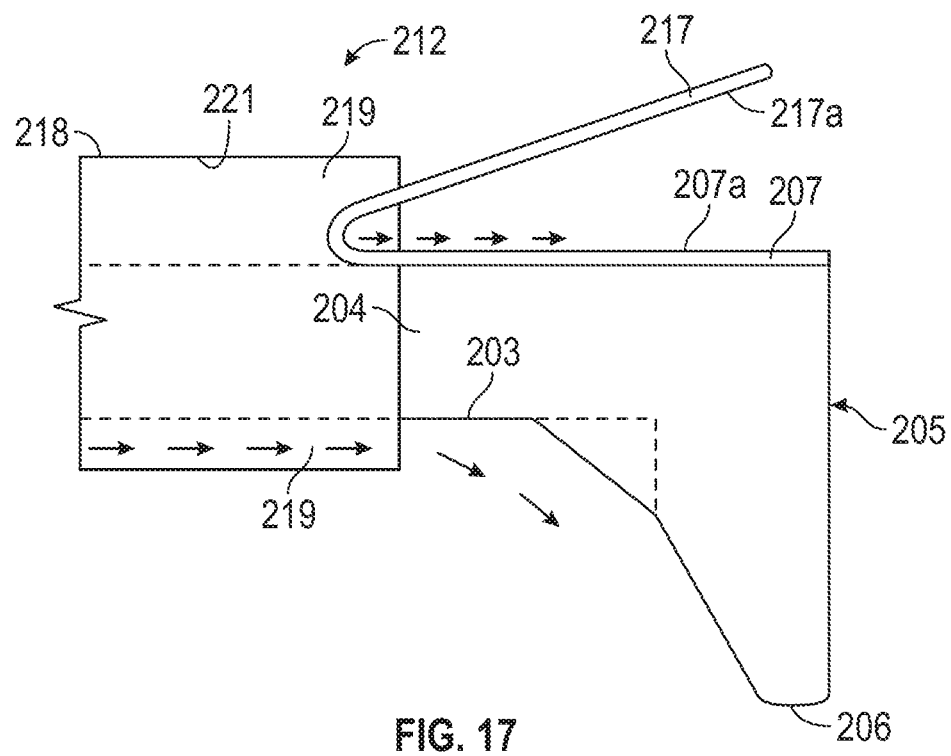
FIG. 17 shows a front view of a device according to embodiments of the present disclosure.

As shown in FIG. 17, a device 212 may have a platform 205 having an extension member 217. Platform 205 has a front tip 206 and a back end 207. Platform 205 may have similar features as platform 5, with the addition of the extension member 217. Device 212 may include a slidable sleeve 218 disposed over a shaft 204 and configured to slide back and forth over an external shaft surface 203 of the shaft 204. The sleeve 218 may be sized and shaped to provide a fluid flow channel 219 between the shaft surface 203 and an inner sleeve surface 221. The fluid flow channel 219 may be configured to deliver a local balanced salt solution, a medication, viscoelastics (e.g. OVD) or therapeutic agents to the site or to wash away reflux of blood, for example.

The extension member 217 may be flexibly coupled to the back end 207 of the platform 205. The extension member 217 may be an integral portion of the platform 205 that extends outward in an angled position. For example, the extension member 217 may be biased in an open position as show in FIG. 17 and configured to be forced towards a closed position when the sleeve 218 is slidably moved towards the platform 205, thus applying a force on the extension member 217, the force directed inward towards the back end 207. Thus, the extension member 217 may be configured as a grasper (e.g., tweezers) to grasp tissue. Similarly, the sleeve 218 may be slidably moved on the shaft 204 away from the platform 205 and a biasing force on the extension member 217 may cause the extension member to move (e.g., open, spring back) to release the tissue.

The extension member 217 may be sized and shaped to essentially mirror the opposing portion of the back end 207 of the platform 205. In an aspect of the disclosure, the device 212 may have multiple extension members 217 spaced apart around the perimeter of the shaft 204. Here, the multiple extension members 217 may each be configured to move in towards the shaft 204 or platform 205 when the slidable sleeve 218 is moved towards the platform 205. Thus, each extension member 217 may be configured to grasp a different portion of tissue or an object.

The back end 207 may have a surface 207a the extension member 217 may have a surface 217a. A portion or all of surface 207a and/or surface 217a may be a sharpened cutting surface. For example, one of the surfaces 207a, 217a may be unsharpened and the other of the surfaces 207a, 217a may be sharpened, or both surfaces 207a, 217a may be sharpened, thus providing a cutting function on the back end 207 of the platform 205. As another example, both surfaces 207a, 217a may be unsharpened, thus providing a grasping function to the back end 207 of the platform 205.

Figure 18A:
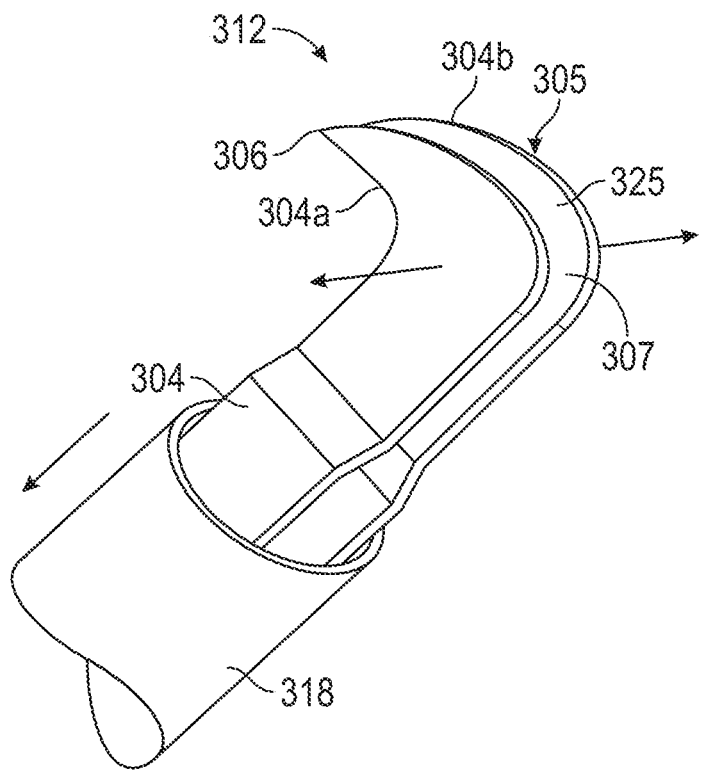
FIG. 18A shows a perspective view of a device in an open position according to embodiments of the present disclosure.
Figure 18B:
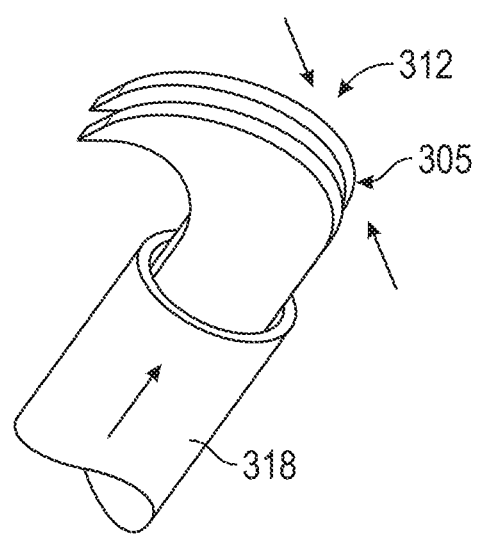
FIG. 18B shows a perspective view of the device of FIG. 32A in a closed position according to embodiments of the present disclosure.

As shown in FIGS. 18A and 18B, a device 312 may have a shaft 304 and a platform 305 having a front tip 306 and a back end 307. The shaft 304 may be split into two shaft sections 304a and 304b. The shaft sections 304a, 304b may be biased away from each other in a non-triggered or default position so that a gap 325 is disposed between the shaft sections 304a, 304b. This non-triggered position may occur when a movable sleeve 318 is pulled away from the platform 305, as shown in FIG. 18A. When the slidable sleeve 318 is moved towards the platform 305 (e.g., activated, triggered), the sleeve 218 may exert a force on the shaft sections 304a, 304b so that the shaft sections 304a, 304b move towards each other, as shown in FIG. 18B. The movement of shaft sections 304a, 304b towards each other may provide a grasping function, allowing the split shaft 304 to grasp tissue or an object. As another example, the movement of shaft sections 304a, 304b towards each other may provide a cutting function, allowing the split shaft 304 to cut tissue or an object. The platform 305 may otherwise have similar structures and/or functions as platform 5.

Figure 19A:
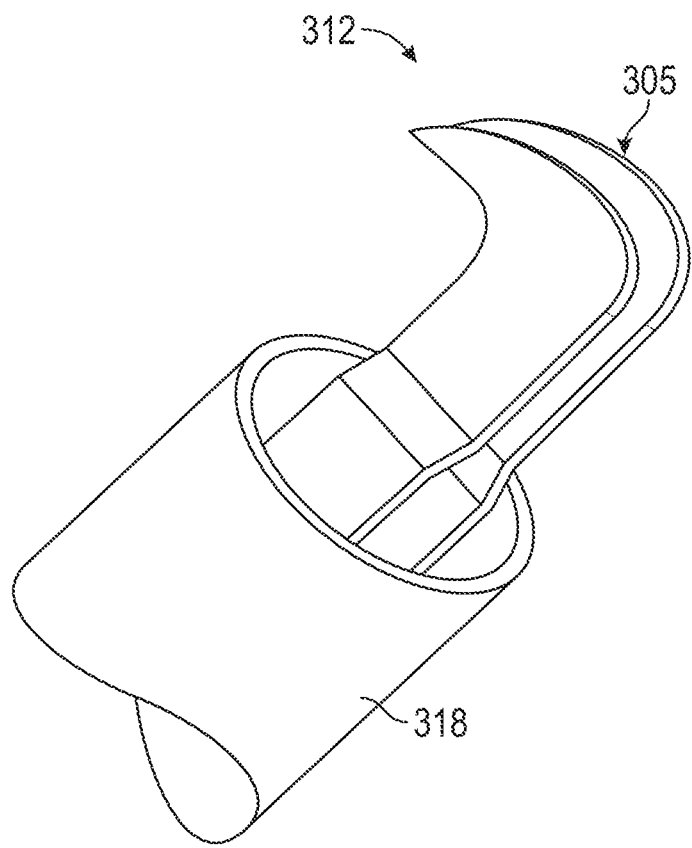
FIG. 19A shows a perspective view of a device in a sheathed position according to embodiments of the present disclosure.
Figure 19B:
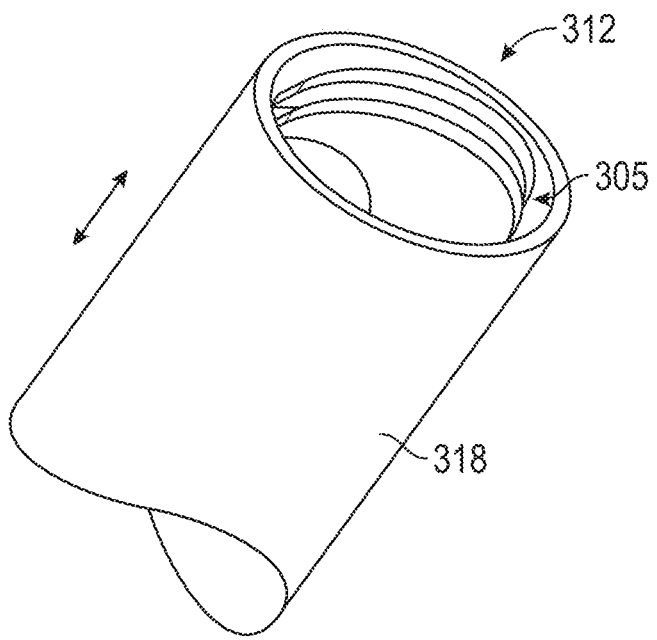
FIG. 19B shows a perspective view of the device of FIG. 33A in an unsheathed position according to embodiments of the present disclosure.

As also shown in FIGS. 18A and 18B, the platform 305 and/or the sleeve 318 may be sized and shaped such that the sleeve 318 is not configured to slide over the entire platform 305. Here, at the fully closed position of the device 312 shown in FIG. 18B, the sleeve 318 extends over just a portion of the platform 305 or none of the platform 305 at all. In some aspects of the disclosure, the sleeve 318 may be sized and shaped to fit completely over the platform in a sheathed or closed position, as shown in FIG. 19A, and to slidably move away from the platform 305 to an unsheathed or open position to expose the platform 305, as shown in FIG. 19B.

As shown in FIGS. 20A and 20B, a device 412 may have a shaft 404 and a platform 405 having a front tip 406 and a back end 407. The platform 405 may have similar features as any of platforms 5, 105, 205, 305. A sleeve 418 is configured to slidably move over shaft 404. Sleeve 418 may include an extension member 417 that is configured to push tissue down onto blades 410, 411 of the platform 405 to cut or shear the tissue. The extension member 417 may be sized and shaped to fit between the blades 410, 411 to improve the cutting of tissue when the sleeve 418 is moved to a closed position shown in FIG. 20A. For example, the extension member 417 may be a short finger that is configured to push tissue down onto the blades 410, 411 as the device 412 is moved through a tissue site. As another example, the extension member 417 may be sized and shaped (e.g., long finger) to provide for grasping tissue or an object between the extension member 417 and a front portion of the platform 405.

Devices 112, 212, 312, 412 may be configured to have any desired shape shaft 104, 204, 304, 404 and sleeve 118, 218, 318, 418. For example, the shaft 104, 204, 304, 404 may be cylindrical (e.g., circular cross-section) and the sleeve 118, 218, 318, 418 may be shaped similarly to match. In aspects of the disclosure, the shaft 104, 204, 304, 404 and sleeve 118, 218, 318, 418 may be oval shaped, egg shaped, and the like. The sleeve 118, 218, 318, 418 may be sized and shaped to be form fitting with the shaft 104, 204, 304, 404. For example, the sleeve 118, 218, 318, 418 may be shaped to just fit around the shaft 104, 204, 304, 404 (e.g., form fit). A form fit sleeve 118, 218, 318, 418 may not have a fluid flow channel between the shaft 104, 204, 304, 404 and the sleeve 118, 218, 318, 418. In another example, the sleeve 118, 218, 318, 418 may be shaped differently than the shaft 104, 204, 304, 404, such as a circular shaft 104, 204, 304, 404 and an elliptical sleeve 118, 218, 318, 418. The sleeve 118, 218, 318, 418 may be formed from one or more materials to be rigid or substantially rigid (e.g., metal).

Figure 22:
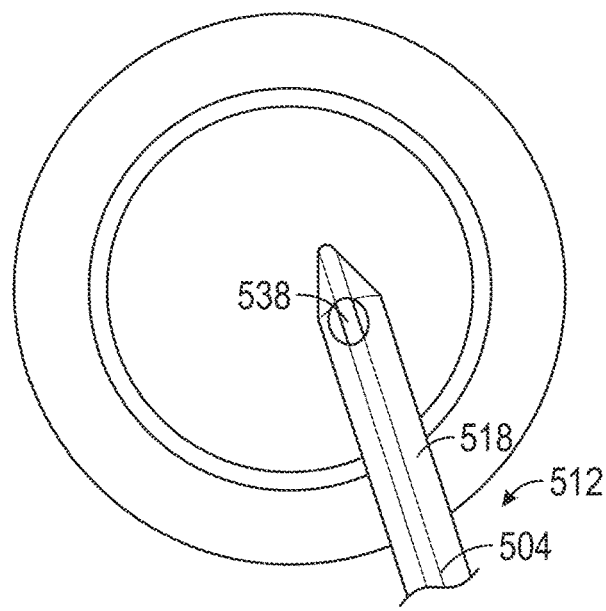
FIG. 22 shows a perspective view of a device with a sleeve aspirating an eye according to embodiments of the present disclosure.

As shown in FIG. 22, a device 512 having a sleeve 518 may be used to aspirate biologic material (e.g., blood, tissue) from an eye. Here, irrigation fluid may flow through the sleeve 518 and exit through one or more ports 538. The aspiration may be provided by a suction force pulling the biologic material back through a hollow portion (e.g., lumen) of a shaft 504. The sleeve 518 may be any desired material (e.g., silicone).

Figure 23:
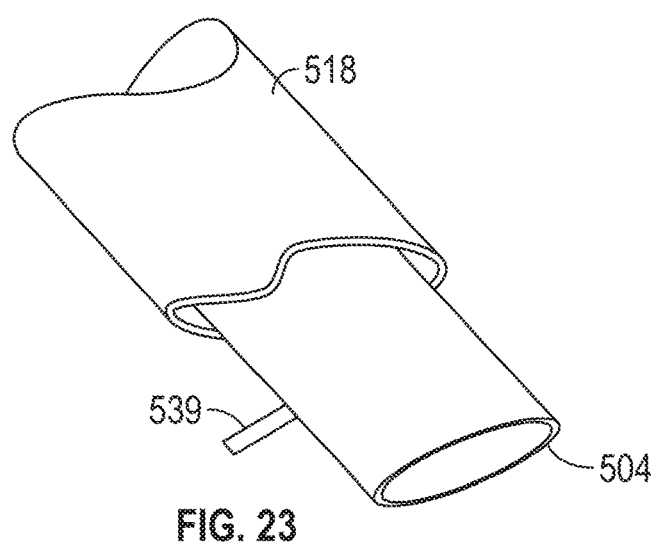
FIG. 23 shows a perspective portion view of a device according to embodiments of the present disclosure.

As shown in FIG. 23, the shaft 504 may have an engagement member 539 configured to stop the sleeve 518 from sliding further up the shaft 504. For example, the engagement member 539 may project outward from the shaft 504, where the engagement member 539 may be a pin, a disc, a ridge, and the like. The engagement member 539 may be retractable such that the engagement member 539 may prevent the sleeve 518 from sliding further up the shaft 504 when in an engagement position and the engagement member 539 may allow the sleeve 518 to slide further up the shaft 504 when in a retracted position.

In one or more embodiments, any of devices 112, 212, 312, 412 may be disposed within sleeve 518. For example, sleeve 118, 218, 318, 418 may be a rigid metal cannula and sleeve 518 may be a flexible silicone sleeve disposed over the rigid metal sleeve 118, 218, 318, 418 and have an opening at an end of the sleeve 518 from which a platform 5, 105, 205, 305 may be extended. As an example, the sleeve 518 may provide a fluid circuit configured to provide fluid flow out of ports 538, where the fluid flows in a space between the sleeve 518 and the sleeve 118, 218, 318, 418, and fluid and/or tissue flow back through the device 112, 212, 312, 412.

III. Construction Materials

It is not intended that embodiments of the invention be limited to any particular construction material; however, it is believed that preferred materials include titanium, stainless steel, polyether ether ketone (PEEK), ceramics, rigid plastics, shape memory alloy such as nitinol, and shape memory polymers. In some embodiments, the platform is made of silicon or another polymer or a hydrogel.

In some embodiments, the knives as contemplated herein may be made of a material that is transparent to optical coherence tomography (OCT) wavelengths (e.g. m typically 800-1600 nm). In one embodiment, an OCT transparent material includes, but is not limited to glycol modified poly(ethylene terephthalate), polyvinyl chloride, poly(methyl methacrylate), or polyphenylsulfone. Although it is not necessary to understand the mechanism of an invention, it is believed that these materials allow the performance of intraoperative OCT during intraocular surgery without any visual interference by the ophthalmic knife.

In one embodiment, the present device is made from metal alloy materials described by Furst, J. G. et al. "Metal Alloys for Medical Devices," U.S. Pat. No. 7,648,591 [40], Richter, K. "Amorphous Metal Alloy Medical Devices," U.S. Pat. No. 7,955,387 [41], all herein incorporated by reference. In one embodiment, the present device is made from a shape memory polymer materials described by Reimink, M. S. and Ogle, M. F. "Medical Devices with Polymer/Inorganic Substrate Composites," U.S. Pat. No. 7,604,663 [42], Langer, R. S. and Lendlein, A. "Shape Memory Polymers," U.S. Pat. No. 6,388,043 [43], Langer, R. S. and Lendlein, A. "Shape Memory Polymers," U.S. Pat. No. 6,720,402 [44], Tong, T. H. "Shape Memory Styrene Copolymer," U.S. Pat. No. 6,759,481 [45], Stalker, K. C. B. et al. "Variable Stiffness Medical Devices," U.S. Pat. No. 7,632,303 [46], Anthamatten, M. L. and Li, J. "Shape Memory Polymers," U.S. Pat. No. 7,935,131 [47], and Berger, E. J. et al. "Methods of Forming a Part Using Shape Memory Polymers," U.S. Pat. No. 8,038,923 [48], all herein incorporated by reference. In some embodiments, the device of the current invention is rigid at room temperature, but is more flexible at body temperature. In some embodiments, the portions of the device of the current invention are rigid at room temperature, but are more flexible at body temperature. In some embodiments, portions of the device are made from different materials. In some embodiments, portions of the device are made from materials of various rigidity. In one embodiment, said shaft is flexible. In some embodiments, said shaft is made from a lower density material.

It is not intended that embodiments of the invention be limited to any particular construction material; however, it is believed that preferred materials include titanium, stainless steel, polyether ether ketone (PEEK), shape memory alloy, and shape memory polymers. In some embodiments, the device of the current invention is rigid at room temperature, but is more flexible at body temperature. In some embodiments, the portions of the device of the current invention are rigid at room temperature, but are more flexible at body temperature. In some embodiments, portions of the device are made from different materials. In some embodiments, portions of the device are made from materials of various rigidity. In one embodiment, said tool shaft 3 is flexible. In some embodiments, said shaft is made from a lower density material.

C. Methods of Using the Multi-Blade Ophthalmic Knifes

In one embodiment, the present invention contemplates, a method for using an ophthalmic knife, comprising: a) providing an ophthalmic knife selected from the group consisting of a dual platform/dual blade ophthalmic knife, a quad-blade ophthalmic knife, an ultrasonic ophthalmic knife, a pincer ophthalmic knife, a gripping ophthalmic knife, a lancet ophthalmic knife, an axial blade ophthalmic knife and a V-blade ophthalmic knife; b) advancing said ophthalmic knife through an incision to a tissue target site; and c) cutting a strip of tissue from said target site.

Detailed Differences Between the Devices

It is not intended that embodiments of the invention be limited to any particular method, medical target, or device confirmation; however, it is believed that the device may be optimally designed to remove trabecular meshwork of the eye, unroofing small vessels (such as veins, arteries, lymphatic vessels, or other vessel with a lumen), and for creating a hole or opening in the tympanic membrane of the ear. It is not intended that embodiments of the invention be limited to any particular mechanism; however, it is believed that creating an opening in the tympanic membrane of the ear may help aid in treating ear disease.

It is not intended that embodiments of the invention be limited to any particular endoscope, it is believed that the device may be optimally designed for an ophthalmic endoscopy system endoscope. One such system is commercially called "Endo Optiks."

Thus, specific compositions and configurations of multiple blade cutting systems have been disclosed. It should be apparent, however, to those skilled in the art that many more modifications besides those already described are possible without departing from the inventive concepts herein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

EXPERIMENTAL

Approval for a preclinical study [49] was obtained from the Colorado Multiple Institutional Review Board for the use of human material prior to initiation of the study and the tenets of the Declaration of Helsinki were followed. Informed consent was obtained from donors or relatives for use in research by the eye bank from which human globes were obtained.

Example I

Histological Analysis

Six (6) corneal rim specimens were obtained from the Rocky Mountain Lions Eye Bank (Aurora, Colo., USA) and the San Diego Eye Bank (San Diego, Calif., USA). Tissue samples were removed from the storage medium and mounted on a platform with the TM side facing up and secured in place using tissue pins. A total of 2 samples were used for each of the 3 treatment methods studied. An MVR blade was used to incise the central TM under microscopic visualization along the length of 2 corneal rims. For the Trabectome® device, the foot plate of the device tip was inserted into the Schlemm's canal under microscopic visualization. Once in place, the foot pedal was used to apply continuous ablation while advancing the tip slowly across the extent of the TM sample. A standard power setting of 0.8 W was used during treatment. A dual-blade device was used to incise the TM of 2 samples. The blade tip was used to incise TM in a manner similar to that used for goniotomy and the blade was then advanced in a clockwise fashion along the extent of the TM. At the distal end, the blade tip was tilted upwards to incise a complete ribbon of TM and the process was repeated in a counterclockwise fashion to incise the remaining TM tissue.

All tissue samples were then immediately preserved in 4% paraformaldehyde/phosphate-buffered saline overnight at 4° C. and then radially cut into quadrants. Rim sections were processed for histology and embedded into paraffin so that the cut edge of the tissue was facing the front of the block. Tissue sections (6 mm thick) were cut and stained with Mayer's hematoxylin-eosin Y (Richard-Allan Scientific, Kalamazoo, Mich., USA). Bright-field imaging was performed using a Nikon Eclipse 80i microscope (Nikon, Melville, N.Y., USA) equipped with a Nikon D5-Fil color camera and a Nikon CFI 103/Plan Fluor objective lens.

Example II

Human Eye Perfusion

A total of 12 human globes from pseudophakic donors with no history of glaucoma were obtained from various eye banks around the country for perfusion studies on each device. The perfusion system used a standard programmable syringe pump (Pump 11 Plus; Harvard Apparatus, Holliston, Mass., USA). Pressure was monitored via an in-line real-time pressure transducer (Research Grade Pressure Transducer; Harvard Apparatus) connected to a single-channel chart recorder (Pharmacia REC-481; Pharmacia/Pfizer New York, N.Y., USA). Polyethylene tubing with a 1.14 mm inner diameter (PE-160; Warner Instruments, Hamden, Conn., USA) was used for all connections.

In each case, the human globe was first prepared by injecting Dulbecco's modified Eagle medium (DMEM; Invitrogen/Life Technologies, Carlsbad, Calif., USA) through the optic nerve with a 26-gauge needle until the globe had returned to a spherical shape. The perfusion line (terminating in another 26-gauge needle) was inserted diagonally through the anterior chamber of the eye, passing through the cornea and pupil and ending with the tip beneath the iris. The globe was surrounded by damp gauze and the perfusion pump (filled with DMEM) was set to an initial inflow rate of 7 mL/min IOP was allowed to increase until it reached 30 mm Hg. The infusion rate was then reduced to 2-5 mL/min to maintain a steady-state IOP for at least 60 minutes prior to TM incision. A preoperative IOP was measured immediately prior to incision in each case. A 1.7 mm stainless steel keratome blade (BD) was used create a tri-beveled clear corneal incision near the limbus, and the anterior chamber was filled with enough viscoelastic (HealonGV; Abbott Medical Optics, Abbott Park, Ill., USA) to maintain the anterior chamber and provide adequate visualization during the procedure in each case. Each technique was performed under gonioscopic view using a standard direct gonioscope with microscope assistance. The surgical procedure used for each device is described above. In each case, approximately 100-180 degrees of TM was treated. For each device, treatment was started 180 degrees away from the corneal wound and extended along the angle in a clockwise direction. The device was then extended in a counterclockwise direction from the same starting point. Every effort was made to treat the maximum amount of degrees possible with each device.

In the case of a conventional modified dual-blade device and a Trabectome®, the instrument was rotated 180 degrees after the initial pass to direct the device tip in the direction of treatment. TOP was allowed to reach a steady state before measuring the postprocedure TOP. Each of the 3 studied surgical techniques was performed on a total of 4 eyes.

Two corneal rim sections were analyzed for each device. Six-micron-thick histologic sections were taken from various clock hours treated with each device and stained with Mayer's hematoxylin-eosin Y (Richard-Allan Scientific). Findings were consistent across all sections from each device tested. Cuts with the MVR blade exhibited complete incision through the entire thickness of TM tissue. However, there was minimal removal of TM with large leaflets of tissue remaining over the Schlemm's canal. The incision extended deeply through the Schlemm's canal with obvious injury to the adjacent deep sclera in the majority of sections (FIG. 1). The Trabectome® also achieved an opening through the entirety of TM tissue into the Schlemm's canal. Although the device also removed a large portion of the central TM, significant leaflets of residual tissue still remained. The residual TM demonstrated extensive charring from thermal injury. Tissue debris was also noted to be occluding distal collector channels (FIG. 2). Tissue incised with the dual-blade device demonstrated a more complete removal of TM without collateral damage (FIG. 3).

Data from human eye perfusion studies are included in Table 1. The extent of TM treatment varied between devices and between eyes from 100 to 180 degrees. All 3 treatment modalities achieved a significant reduction in measured IOP 30 minutes after treatment. Treatment with the dual-blade device and Trabectome® resulted in a mean TOP reduction of 40% each, whereas the MVR blade achieved a 31% reduction. Although the percentage of TOP decrease was greater for Trabectome® and the dual-blade device, there was no statistically significant difference in the TOP lowering between devices (dualblade/MVR P=0.13; dual-blade/Trabectome® P=0.96; Trabectome®/MVR P=0.12). There was no correlation between the number of degrees of TM treated and the percentage TOP change for any device ($r2=0.077-0.271$).

TABLE 1

Human Eye Perfusion Studies After Treatment of Trabecular Meshwork by Various Conventional Devices

|  | Eye | Degree of Angle Treated | Preprocedure IOP | Postprocedure IOP | Absolute IOP Change | Percent IOP Change | P Value |
| --- | --- | --- | --- | --- | --- | --- | --- |
| Modified Dual-blade device | 1 | 140 | 17 | 10 | −7 | −41 |  |
|  | 2 | 180 | 19 | 11 | −8 | −42 |  |
|  | 3 | 130 | 15 | 9 | −6 | −40 |  |
|  | 4 | 180 | 22 | 14 | −8 | −36 |  |
|  | Mean | 157.5 ± 26.3 | 18.3 ± 3.0 | 11.0 ± 2.2 | −7.3 | −40 | 0.00063 |
| MVR blade | 1 | 180 | 20 | 14 | −6 | −30 |  |
|  | 2 | 180 | 20 | 15 | −5 | −25 |  |
|  | 3 | 150 | 18 | 12 | −6 | −33 |  |
|  | 4 | 170 | 16 | 10 | −6 | −38 |  |
|  | Mean | 170.0 ± 14.1 | 18.5 ± 1.9 | 12.8 ± 2.2 | −5.8 | −31 | 0.00018 |
| Trabectome ® | 1 | 120 | 18 | 12 | −6 | −33 |  |
|  | 2 | 130 | 21 | 12 | −9 | −43 |  |
|  | 3 | 100 | 17 | 11 | −6 | −35 |  |
|  | 4 | 120 | 19 | 10 | −9 | −47 |  |
|  | Mean | 117.5 ± 12.6 | 18.8 ± 1.7 | 11.3 ± 1.0 | −7.5 | −40 | 0.00324 |

IOP = intraocular pressure;
MVR = microvitreoretinal.

In the study, the initial preclinical evaluation of an embodiment of the present invention, a dual-blade device for the treatment of glaucoma, is presented [49]. Histologic analysis of human cadaver eye tissue treated with the dual-blade device achieved more complete removal of TM tissue while avoiding any discernible damage to surrounding tissue. Treatment with other methods of TM removal such as MVR blade goniotomy and ab intern trabeculectomy with the Trabectome® device failed to attain equivalent histologic results to the novel dual-blade device. While histology data were obtained from ex vivo-treated corneal rims, similar findings were noted when treatment was performed using the ab intern approach on perfused eyes. The near-absence of TM leaflets with the dual-blade device may be beneficial in reducing the chances of future physical obstruction, and the lack of tissue damage may also reduce the inflammatory response or subsequent fibrosis at the surgical site.

In addition to potentially favorable histologic outcomes, the dual-blade device resulted in significant TOP lowering in a human eye perfusion model. Although all 3 devices yielded similar immediate reduction in TOP after use in a perfusion model, it is unclear how a more complete removal of TM tissue and decreased collateral damage with the dual-blade device of the present invention will translate into long term surgical outcomes when used to treat glaucoma. No correlation was found between degrees of TM treated and TOP reduction. It is plausible that TOP reduction may depend more on the number of downstream collector channels exposed rather than the absolute amount of TM removal alone.

Figure 4A:
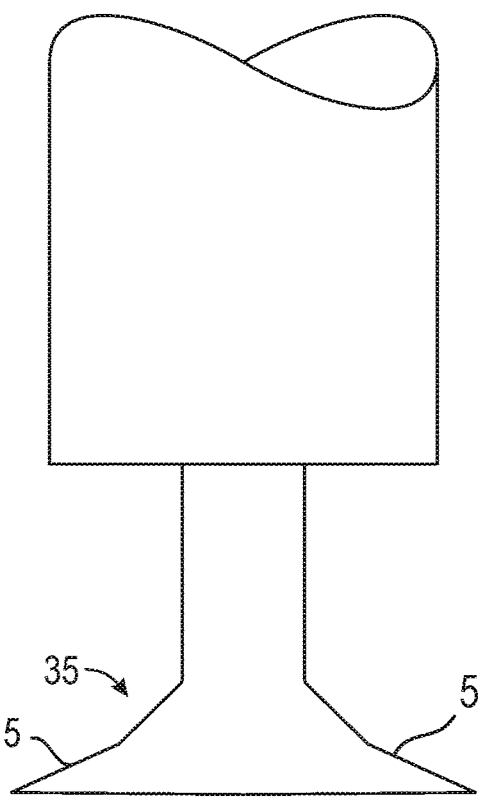
FIGS. 4A, B, & C present exemplary embodiments of a dual platform/dual blade ophthalmic knife.
Figure 4B:
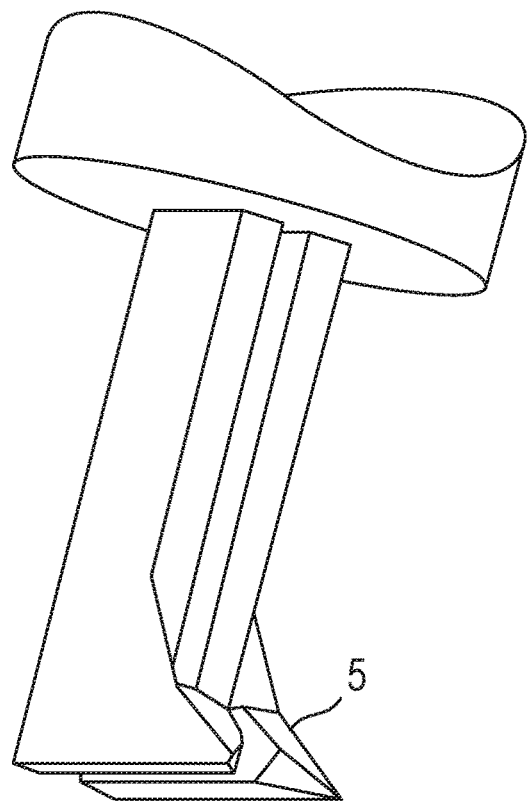
FIG. 4B depicts a parallel configuration of two platforms.
Figure 4C:
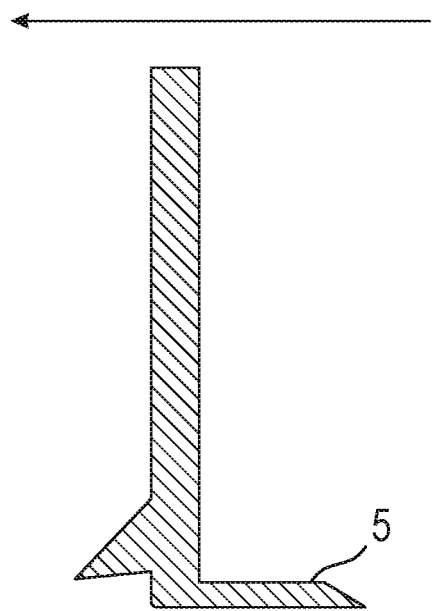
FIG. 4C depicts an offset configuration of the first and second platforms.
Figure 5:
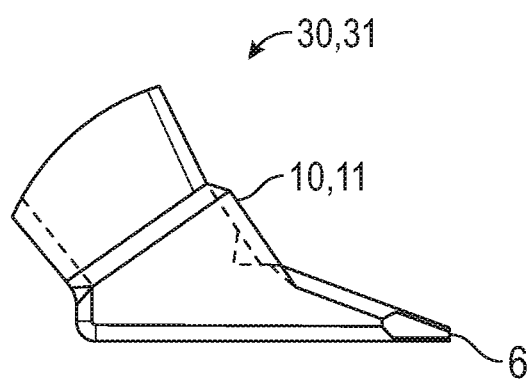
FIG. 5 presents an exemplary embodiment of quad-blade ophthalmic knife comprising two platform blades (10 and 11) and two shaft blades (30 and 31). In one embodiment, the two upper (shaft) blades positioned above the lower (platform) blades, the upper and lower blades being able to move up and down to cut TM between the upper and lower blades (like scissors on either side of the ramp). In one embodiment, the tipper blades may be moved by triggering a mechanism, such as squeezing the handle (like MST forceps).

In an effort to provide a low-cost MIGS device that can be widely used by ophthalmic surgeons, one embodiment of the present invention contemplates a novel medical-grade stainless steel dual-blade device that can successfully remove TM with no discernible collateral damage was designed. In one embodiment, the device comprises a unique dual-edge blade design using precise geometries to allow for more complete removal of TM tissue (FIGS. 4A&B). Although it is not necessary to understand the mechanism of an invention, it is believed that the procedure is performed from an ab intern approach and is viscoelastic to maintain the anterior chamber. For example, the size and tip of the blade can allow for a smooth entry into the Schlemm's canal, similar to techniques used for traditional goniotomy procedures. Once in place, the tip is advanced through the Schlemm's canal and the TM is elevated along a designed ramp that guides tissue toward a set of blades positioned specifically to incise and remove TM. In contrast to the Trabectome® footplate, which is juxtaposed between the outer wall of the Schlemm's canal and the inner wall of the Schlemm's canal to provide protection during cautery, the dual-blade device transects TM and elevates TM off of the outer wall of the Schlemm's canal. Although it is not necessary to understand the mechanism of an invention, it is believed that by elevating the TM along the ramp of the device as it moves forward leads to maximal tissue removal when incised by the superiorly placed and strategically angled dual blades. It is further believed that the angle between the distal cutting edge and the handle is engineered to allow maximal angle treatment through 1 incision while avoiding trauma to the cornea above or the scleral spur below. The excised TM may then be removed from the eye with forceps or aspirated during the irrigation/aspiration phase if combined with cataract extraction. In addition, the device of the present invention can easily pass through clear corneal incisions as small as 1.2 mm, thus obviating the need for additional incisions when coupled with phacoemulsification.

Example III

Traditional Incisional Goniotomy

This procedure begins with an incision in trabecular meshwork extending into sclera with large segments of trabecular meshwork. For this procedure (considered the gold standard surgery for "cutting" through the trabecular meshwork and traditionally called "goniotomy") an MVR blade was used to incise the trabecular meshwork to create an opening into Schlemm's canal. A histological sample was provided from a procedure in which an incision exists through Trabecular meshwork and extends into sclera. There were large leaflets of trabecular meshwork remaining on either side of the incision. These leaflets scar down and close the opening that was created into Schlemm's canal. This preludes any long-term benefit in intraocular pressure lowering which is the goal of the surgery.

Example IV

Trabectome® Procedures

For this procedure (designed to replace goniotomy and to improve upon that procedure by removing sections of trabecular meshwork), a Trabectome® device was used to engage the trabecular meshwork and cautery was applied to the trabecular meshwork. The circle shows an area where a small segment of trabecular meshwork was removed; however, there are large leaflets of trabecular meshwork remaining and charred tissue on either side of the treatment area. Post Trabectome® treatment showed trabecular meshwork remnants and charring of tissue. Tissue debris is occluding a collector channel this device "burns" tissue and the burning of tissue creates inflammation that leads to more scar formation that leads to failure of the surgically induced opening into Schlemm's canal. In addition, due to cautery, many bubbles are formed during the procedure that makes visualization difficult during the actual procedure. These issues do not occur with the current invention device, which is a major advantage.

REFERENCES

1. Quigley, H. A. and Broman, A. T. (2006) "The Number of People with Glaucoma Worldwide in 2010 and 2020," *Br. J. Ophthalmol.* 90(3), 262-267.
2. Grant, W. M. (1951) "Clinical Measurements of Aqueous Outflow," *A.M.A. Archives of Ophthalmology* 46(2), 113-131
3. Grant, W. (1963) "Experimental Aqueous Perfusion in Enucleated Human Eyes," *Arch. Ophthalmol.* 69(6), 783-801.
4. Johnson, D. H. and Tschumper, R. C. (1987) "Human. Trabecular Meshwork Organ Culture. A New Method," *Invest. Ophthalmol. Vis. Sci.* 28(6), 945-953.
5. Herschler, J. and Davis, E. B. (1980) "Modified Goniotomy for Inflammatory Glaucoma. Histologic Evidence for the Mechanism of Pressure Reduction," Arch. Ophthalmol. 98(4), 684-687.
6. Luntz, M. H. and Livingston, D. G. (1977) "Trabeculotomy Ab Externo and Trabeculectomy in Congenital and Adult-Onset Glaucoma," *Am. J. Ophthalmol.* 83(2), 174-179.
7. Anderson, D. R. (1983) "Trabeculotomy Compared to Goniotomy for Glaucoma in Children," *Ophthalmology* 90(7), 805-806.
8. Jea, S. Y. et al. (2012) "Ab Interno Trabeculectomy Versus Trabeculectomy for Open-Angle Glaucoma," *Ophthalmology* 119(1), 36-42.
9. Minckler, D. S. et al. (2005) "Clinical Results with the Trabectome® for Treatment of Open-Angle Glaucoma," *Ophthalmology* 112(6), 962-967.
10. Pantcheva, M. B. and Kahook, M. Y. (2010) "Ab Interno Trabeculectomy," *Middle East Afr. J. Ophthalmol.* 17(4), 287-289.
11. Francis, B. A. et al. (2006) "Ab Intern® Trabeculectomy: Development of a Novel Device (Trabectome®) and Surgery for Open-Angle Glaucoma," *J. Glaucoma* 15(1), 68-73.
12. Kahook, M. Y. "Modified Dual-Blade Cutting System," U.S. Provisional Patent Application 61/637,611, filed Apr. 24, 2012. (published N/A).
13. Tan, Y. et al. (2011) "Postoperative Complications after Glaucoma Surgery for Primary Angle-Closure Glaucoma Vs Primary Open-Angle Glaucoma," *Arch. Ophthalmol.* 129(8), 987-992.
14. Sorensen, J. T. et al. "Tubular Cutter Device and Methods for Cutting and Removing Strips of Tissue from the Body of a Patient," U.S. Pat. No. 7,959,641, application Ser. No. 10/560,267, filed Jun. 10, 2004. (issued Jun. 14, 2011).
15. Sorensen, J., T. et al. "Tubular Cutting Device for Cutting and Removing Tissue," WIPO PCT Patent Publication Number WO/2004/110501, Application PCT/US2004/018488, filed Jun. 10, 2004. (published Dec. 23, 2004).

16. Sorensen, J. T. et al. "Tubular Cutter Device and Methods for Cutting and Removing Strips of Tissue from the Body of a Patient," United States Patent Application Publication Number US 2007-0276420 A1, application Ser. No. 10/560,267, filed Jun. 10, 2004. (published Nov. 29, 2007).
17. Huculak, J. C. "Small Gauge Mechanical Tissue Cutter/Aspirator Probe for Glaucoma Surgery," United States Patent Application Publication Number US 2009-0287233 A1, application Ser. No. 12/120,867, filed May 15, 2008. (published Nov. 19, 2009).
18. Baerveldt, G. and Chuck, R. "Minimally Invasive Glaucoma Surgical Instrument and Method," United States Patent Application Publication Number US 2011-0077626 A1, application Ser. No. 12/843,458, filed Jul. 26, 2010. (published Mar. 31, 2011).
19. Baerveldt, G. and Chuck, R. "Minimally Invasive Glaucoma Surgical Instrument and Method," U.S. Pat. No. 7,785,321, application Ser. No. 11/273,914, filed Nov. 14, 2005. (issued Aug. 31, 2010).
20. Baerveldt, G. and Chuck, R. "Minimally Invasive Glaucoma Surgical Instrument and Method," U.S. Pat. No. 6,979,328, application Ser. No. 10/052,473, filed Jan. 18, 2002. (issued Dec. 27, 2005).
21. Baerveldt, G. and Chuck, R. "Minimally Invasive Glaucoma Surgical Instrument and Method," United States Patent Application Publication Number US 2006-0106370 A1, application Ser. No. 11/273,914, filed Nov. 14, 2005. (published May 18, 2006).
22. Baerveldt, G. and Chuck, R. "Minimally Invasive Glaucoma Surgical Instrument and Method," United States Patent Application Publication Number US 2002-0111608 A1, application Ser. No. 10/052,473, filed Jan. 18, 2002. (published Aug. 15, 2002).
23. Lind, C. and Huculak, J. C. "Small Gauge Mechanical Tissue Cutter/Aspirator Probe for Glaucoma Surgery," WIPO PCT Patent Publication Number WO/2009/140185, Application PCT/US2009/043420, filed May 11, 2009. (published Nov. 19, 2009).
24. Lind, C. and Huculak, J. C. "Small Gauge Mechanical Tissue Cutter/Aspirator Probe for Glaucoma Surgery," European Patent EP 2303203 A1, Application EP 09747269.0, filed May 11, 2009. (published Apr. 6, 2011).
25. Bergheim, 0. B. and Gharib, M. "Apparatus and Method for Treating Glaucoma," WIPO PCT Patent Publication Number WO/2001/078631, Application PCT/US2001/007398, filed Mar. 8, 2001. (published Oct. 25, 2001).
26. Skjaerpe, F. "Microsurgical Instrument," U.S. Pat. No. 4,501,274, application Ser. No. 06/438,891, filed Oct. 29, 1982. (issued Feb. 26, 1985).
27. Skjaerpe, F. "Microsurgical Instrument," European Patent EP 0073803 B1, Application EP 82900833, filed Mar. 12, 1982. (issued Jul. 10, 1985).
28. Conston, S. R. and Yamamoto, R. K. "Ophthalmic Microsurgical System," United States Patent Application Publication Number US 2006-0149194 A1, application Ser. No. 10/496,254, filed Nov. 21, 2002. (published Jul. 6, 2006).
29. Conston, S. R. and Yamamoto, R. K. "Ophthalmic Microsurgical System," WIPO PCT Patent Publication Number WO/2003/045290, Application PCT/US2002/037572, filed Nov. 21, 2002. (published Jun. 5, 2003).
30. Conston, S. R. and Yamamoto, R. K. "Ophthalmic Microsurgical System," European Patent EP 1455698 A1, Application EP 02791298 A, filed Nov. 21, 2002. (published Sep. 15, 2004).
31. Conston, S. R. and Yamamoto, R. K. "Ophthalmic Microsurgical System," Korean Patent KR 1020040058309, Application KR 1020040058309, filed Nov. 21, 2002. (issued Sep. 15, 2004).
32. Conston, S. R. and Kupiecki, D. J. "Ophthalmic Microsurgical Instruments," United States Patent Application Publication Number US 2007-0073275 A1, application Ser. No. 10/555,065, filed Apr. 16, 2004. (published Mar. 29, 2007).
33. Conston, S. R. et al. "Ophthalmic Microsurgical Instruments," WIPO PCT Patent Publication Number WO/2004/093761, Application PCT/US2004/011783, filed Apr. 16, 2004. (published Nov. 4, 2004).
34. Conston, S. R. et al. "Ophthalmic Microsurgical Instruments," European Patent EP 1615604 A1, Application EP 04750224.0, filed Apr. 16, 2004. (published Jan. 18, 2006).
35. Huculak, J. C. et al. "Pulsed Electric Field Probe for Glaucoma Surgery," *United States* Patent Application Publication Number US 2011-0230877 A1, application Ser. No. 12/725,020, filed Mar. 16, 2010. (published Sep. 22, 2011).
36. Jacobi, P. C. et al. (1997) "Technique of Goniocurettage: A Potential Treatment for Advanced Chronic Open Angle Glaucoma," *Br. J. Ophthalmol.* 81(4), 302-307.
37. Jacobi, P. C. et al. (1999) "Goniocurettage for Removing Trabecular Meshwork: Clinical Results of a New Surgical Technique in Advanced Chronic Open-Angle Glaucoma," *Am. J. Ophthalmol.* 127(5), 505-510.
38. Ting, J. L. M. et al. (2012) "Ab Interno Trabeculectomy: Outcomes in Exfoliation Versus Primary Open-Angle Glaucoma," *J. Cataract. Refract. Surg.* 38(2), 315-323.
39. Kahook, M. Y. "Modified Dual-Blade Cutting System," WIPO PCT Patent Publication Number WO/2013/163034, Application PCT/US2013/037374, filed Apr. 19, 2013. (published Oct. 31, 2013).
40. Furst, J. G. et al. "Metal Alloys for Medical Devices," U.S. Pat. No. 7,648,591, application Ser. No. 12/272,317, filed Nov. 17, 2008. (issued Jan. 19, 2010).
41. Richter, K. "Amorphous Metal Alloy Medical Devices," U.S. Pat. No. 7,955,387, application Ser. No. 12/243,741, filed Oct. 1, 2008. (issued Jun. 7, 2011).
42. Reimink, M. S. and Ogle, M. F. "Medical Devices with Polymer/Inorganic Substrate Composites," U.S. Pat. No. 7,604,663, application Ser. No. 09/475,721, filed Dec. 30, 1999. (issued Oct. 20, 2009).
43. Langer, R. S. and Lendlein, A. "Shape Memory Polymers," U.S. Pat. No. 6,388,043, application Ser. No. 09/256,626, filed Feb. 23, 1999. (issued May 14, 2002).
44. Langer, R. S. and Lendlein, A. "Shape Memory Polymers," U.S. Pat. No. 6,720,402, application Ser. No. 10/141,891, filed May 8, 2002. (issued Apr. 13, 2004).
45. Tong, T. H. "Shape Memory Styrene Copolymer," U.S. Pat. No. 6,759,481, application Ser. No. 10/056,590, filed Jan. 24, 2002. (issued Jul. 6, 2004).
46. Stalker, K. C. B. et al. "Variable Stiffness Medical Devices," U.S. Pat. No. 7,632,303, application Ser. No. 10/152,150, filed May 21, 2002. (issued Dec. 15, 2009).
47. Anthamatten, M. L. and Li, J. "Shape Memory Polymers," U.S. Pat. No. 7,935,131, application Ser. No. 11/820,693, filed Jun. 20, 2007. (issued May 3, 2011).
48. Berger, E. J. et al. "Methods of Forming a Part Using Shape Memory Polymers," U.S. Pat. No. 8,038,923, application Ser. No. 12/356,518, filed Jan. 20, 2009. (issued Oct. 18, 2011).

49. Seibold, L. K. et al. (2013) "Preclinical Investigation of Ab Interno Trabeculectomy Using a Novel Dual-Blade Device," *Am. J. Ophthalmol.* 155(3), 524-529.e522.

What is claimed is:

1. A dual-blade ophthalmic knife, comprising:
   a handle;
   a shaft connected to the handle; and
   a platform connected to the shaft, a front portion of the platform extending radially outward from the shaft, wherein the platform comprises:
      a first blade;
      a second blade;
      an anterior blade tip;
      an extension member extending from a back end of the platform opposing the front end of the platform and radially outward from the shaft, wherein the extension member is configured as a grasping feature; and
   a movable sleeve configured to slideably move along the shaft and to grasp tissue between the sleeve and the grasping feature.

2. The ophthalmic knife of claim 1, wherein the grasping feature is a tweezer.

3. The ophthalmic knife of claim 1, wherein the grasping feature is a forceps.

4. The ophthalmic knife of claim 1, wherein the grasping feature comprises a spring biased to close the grasping feature.

5. The ophthalmic knife of claim 1, wherein the anterior blade tip is a retractable blade tip.

6. The ophthalmic knife of claim 1, wherein the first blade and the second blade are respectively attached to a first lateral side and a second lateral side of the platform.

7. The ophthalmic knife of claim 1, wherein the platform comprises a ramp increasing in depth extending from the anterior blade tip to a posterior end.

8. The ophthalmic knife of claim 1, wherein the platform further comprises a first annular cutting edge.

9. The ophthalmic knife of claim 1, wherein a width of the platform is between 0.2 to 0.3 mm.

10. The ophthalmic knife of claim 1, wherein the shaft is a telescoping shaft.

11. The ophthalmic knife of claim 1, wherein the sleeve is configured to overcome a biasing force of the grasping feature by engaging at least a portion of the grasping feature as the sleeve is moved in a direction along the shaft.

12. The ophthalmic knife of claim 1, wherein the handle comprises an activation member coupled to the sleeve, the activation member configured to cause the sleeve to move.

13. The ophthalmic knife of claim 1, wherein at least a portion of the grasping feature comprises a sharpened surface configured to cut tissue.

14. A method for incising a trabecular meshwork to form an opening in trabecular meshwork tissue of an eye having a Schlemm's Canal, an anterior chamber and a trabecular meshwork, the method comprising:
   providing the knife of claim 1;
   inserting the platform into the anterior chamber, the platform including the anterior tip;
   advancing the platform, anterior tip first, through the trabecular meshwork and into the Schlemm's Canal;
   advancing the platform, anterior tip first, through the Schlemm's Canal such that trabecular meshwork tissue contacts and is severed by the first and second blades; and
   grasping the severed trabecular meshwork tissue with the grasping feature.

15. The method of claim 14, wherein the grasping feature is a tweezer.

16. The method of claim 14, wherein the grasping feature is a forceps.

17. The method of claim 14, wherein the grasping feature comprises a spring biased to close the grasping feature.

18. The method of claim 14, wherein the platform of the device further comprises a bottom surface that is transversely concave, wherein the platform is configured so that when the platform is advanced into the Schlemm's Canal, a back wall of the Schlemm's canal is juxtaposed to the bottom surface.

19. The method of claim 14, wherein the handle of the device comprises an activation member, wherein applying a force to the activation member causes the grasping feature to close.

20. The method of claim 14, wherein the handle of the device comprises an activation member, wherein applying a force to the activation member causes the grasping feature to open.

* * * * *